United States Patent [19]
Waugh et al.

[11] Patent Number: 5,353,356
[45] Date of Patent: Oct. 4, 1994

[54] PRODUCT GAUGE METHODS AND APPARATUS FOR USE IN THE OPTICAL DETERMINATION OF THE ACCEPTABILITY OF PRODUCTS

[76] Inventors: Richard M. Waugh, 12332 Winfree St., Chester, Va. 23831; Robert J. Maher, 2919 Glendower Cir., Midlothian, Va. 23113

[21] Appl. No.: 905,898

[22] Filed: Jun. 29, 1992

Related U.S. Application Data

[63] Continuation-in-part of Ser. No. 661,809, Feb. 27, 1991, Pat. No. 5,146,510, which is a continuation-in-part of Ser. No. 308,739, Feb. 9, 1989, Pat. No. 5,046,111.

[51] Int. Cl.[5] .......................... G06K 9/00; H04N 7/00
[52] U.S. Cl. .......................... 382/8; 382/1; 348/92; 348/130; 348/142
[58] Field of Search .......................... 382/1, 6, 8, 48, 30, 382/34; 358/101, 106, 107; 356/71; 364/527; 312/234; G06K 9/00, 9/68, 9/62, 9/20, 9/74; A47B 81/00; G06F 15/52; H04N 7/00

[56] References Cited

U.S. PATENT DOCUMENTS

| | | | |
|---|---|---|---|
| 3,986,244 | 10/1976 | Latanzi | 312/324 |
| 4,202,037 | 5/1980 | Glaser et al. | 364/525 |
| 4,802,093 | 1/1989 | Ema | 382/6 |
| 5,046,111 | 9/1991 | Cox et al. | 382/8 |
| 5,146,510 | 9/1992 | Cox et al. | 382/8 |

*Primary Examiner*—Jose L. Couso

[57] ABSTRACT

A product gauge is disclosed for use in the optical inspection of products. The product gauge can be produced from the image of a model of the product. The product gauge can also be electronically constructed on a video screen by a computer line-drawing program. The product gauge aids in the alignment and the processing of information by the optical inspecting means including aiding an operator in determining whether a product is acceptable. The product gauge can be used to quickly and accurately tailor a generalized product inspection apparatus to specific products and thus ease the change from inspecting one product to another product.

38 Claims, 18 Drawing Sheets

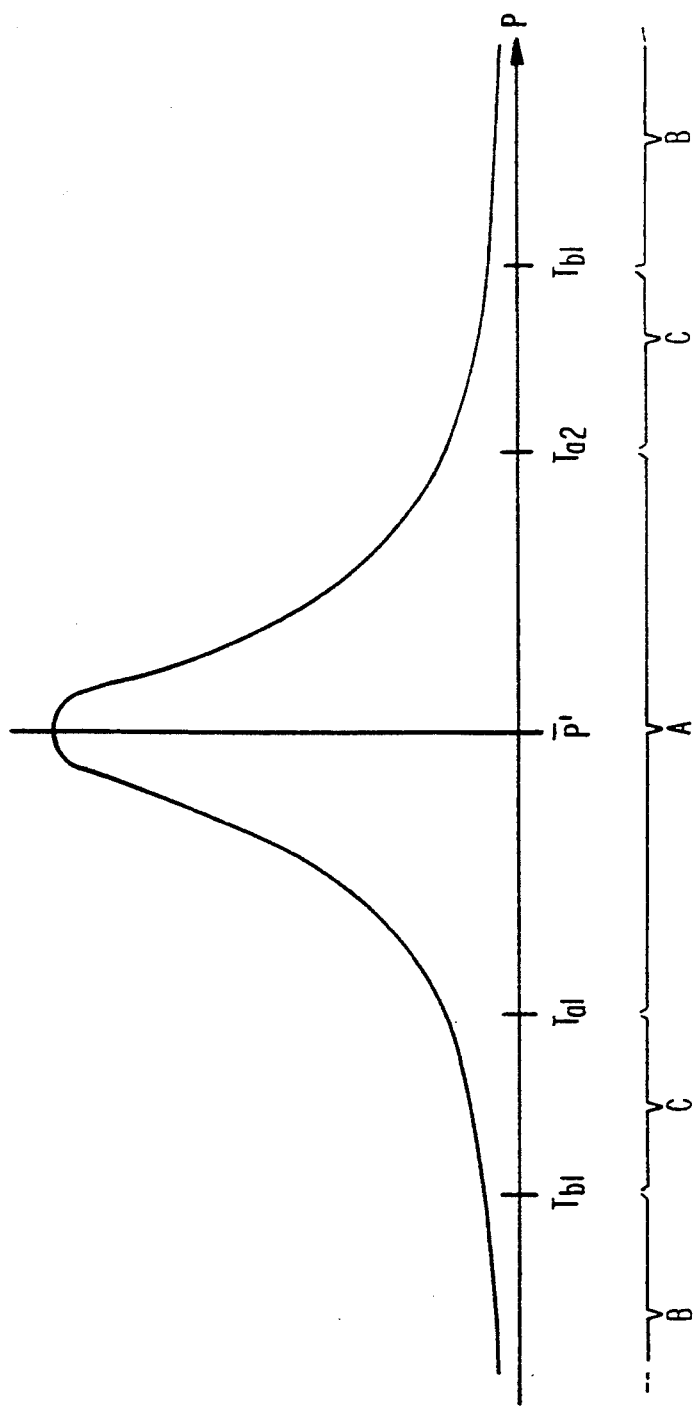

PRODUCT GAUGE METHODS AND APPARATUS FOR USE IN THE OPTICAL DETERMINATION OF THE ACCEPTABILITY OF PRODUCTS

BACKGROUND OF THE INVENTION

This is a continuation-in--part of application Ser. No. 661,809, filed on Feb. 27, 1991, and issued Sep. 8, 1992 as U.S. Pat. No. 5,146,510 which in turn is a continuation-in-part of application Ser. No. 308,739, filed Feb. 9, 1989, and issued Sep. 3, 1991 as U.S. Pat. No. 5,046,111.

This invention relates to product inspection methods and apparatus, and more particularly to methods and apparatus for optically determining whether or not a product has an acceptable appearance. Specifically, methods and apparatus for a product gauge are provided that may be used to enhance the performance of optical product inspection means.

For many products such as consumer goods like packaged foods, beverages, cleaning products, health and beauty aids, cigarettes, cigars, etc., it is very important that the external appearance of the product or its packaging be uniform and defect-free. Yet these products are typically produced in such large quantities and at such high speeds that some form of automated optical inspection is practically essential. Many prior art optical inspection techniques rely on examining only preselected parts of the object being inspected. It is therefore possible for such prior art systems to miss defects occurring in regions other than those preselected for examination, and/or to miss defects of a kind that were not anticipated when the system was set-up. It is highly desirable for an optical inspection system to be able to test all or substantially all parts of the product image so that defects of any kind occurring anywhere in the image can be detected. At the same time the inspection system should not reject products having minor but acceptable deviations from the ideal product.

For even a relatively simple product image such as a cigarette pack, an inspection system must be initially supplied with a tremendous amount of information in order to enable the system to inspect all or substantially all portions of the image with the sophistication required to discriminate between acceptable products (i.e., products having the ideal appearance or an appearance acceptably close to the ideal) and unacceptable products which should be rejected because of defects in appearance or appearance which is not sufficiently close to the ideal. Identifying and entering this information into the inspection system apparatus typically requires a very high level of skill and/or large amounts of operator time. Moreover, this data identification and entry task must be repeated each time a new or even slightly different product is to be inspected.

Prior art optical inspection techniques must also be customized for each product inspection task. This requires a high level of skill and is very time-consuming. Prior art systems were also difficult to align with the products being inspected. This is especially true when the system was applied to a new or different product. It is also true that these product inspection systems require at least some operator or human input. No matter how sophisticated the product inspection system, if the operator or human input was difficult to perform, efficacy of the whole system would be compromised.

In view of the foregoing, it is an object of this invention to provide methods and apparatus, for use with optical product inspection means, which provide a product gauge which aids in the processing of an overall image of the product being inspected so that a significant defect or deviation from the norm occurring anywhere in the image will cause the associated product to be identified as deviant or defective.

It is another object of this invention to provide methods and apparatus, for optical product inspection means, which provide a product gauge which aids in aligning and in information processing by the optical product inspection means It is still another object of this invention to provide methods and apparatus, for optical product inspection means, which provide a product gauge which aids in the universal application of optical product inspection means and which can adapt the optical product inspection means to new inspection tasks without requiring elaborate set-up and monitoring by a highly skilled operator.

It is still another object of this invention to provide optical inspection systems which greatly reduce the level of operator skill and amount of operator time required to set up the system to inspect a new or different product.

It is still another object of this invention to provide methods and apparatus, for optical product inspection means, which provide a product gauge which can enable the optical product inspection means to acquire the information required to perform new inspection tasks without the intervention of a highly skilled operator.

It is still another object of this invention to improve and simplify optical inspection systems.

SUMMARY OF THE INVENTION

These and other objects of the invention are accomplished in accordance with the principles of the invention by providing methods and apparatus which provide a product gauge of objects to be inspected. The product gauge of this invention is constructed to work with optical product inspection means and enhance the efficiency, applicability, and ease of use of those means. The product gauge aids with the alignment of the products and the optical product inspection means, the processing of the image of the products by those means, the human interaction with those means, and the applicability of those means to different or changing products.

The product gauge of this invention may be construed to work with many different product inspection apparatuses that may include optical product inspection means. One such optical product inspection means is the optical inspection system of U.S. application Ser. No. 661,809 filed on Feb. 27, 1991. That application provides optical inspection systems which form an initial discriminant function or "filter" from a composite of a relatively small number of "first phase" images which the operator of the system determines to be acceptable images. The product gauge of this invention can aid the operator in this determination. A relatively simple technique (e.g., a logical OR function) is preferably used to form this composite. The ability to produce the initial discriminant function quickly using such a simple combination of a small number of images facilitates rapid "start-up" of the system. Thereafter the system uses the initial discriminant function to process a relatively large number of representative "second phase" images in order to compute statistical information about the images in relation to the initial discriminant function. In particular, the system uses the initial discriminant function to compute a processed value for each second phase image. These processed values will typically have an approximately normal or Gaussian distribution. The upper and lower limits of a central portion of this distribution containing a first statistically large number of the processed values are identified as first threshold values. The upper and lower limits of a central portion of this distribution containing a second statistically even larger number of the processed values are identified as second threshold values.

In a subsequent third phase of the operation of the system, the first and second threshold values are used in the processing of a relatively large number of "third phase" images. In particular, the system uses a discriminant function (initially the above-mentioned initial discriminant function) to compute a processed value for each successive third phase image. If this processed value for a given third phase image is between the first threshold values, that third phase image is automatically used to refine (e.g., using a Widrow-Hoff-type adaptive training process) the discriminant function for subsequent use. If the processed value for a third phase image is not between the second threshold values, that third phase image is automatically discarded. As a third possibility, if the processed value for a third phase image is not between the first threshold values but is between the second threshold values, the operator of the system is given the choice as to whether or not that image should be discarded (i.e., because the image looks unacceptable) or used to refine the discriminant function for subsequent use (i.e., because the image looks acceptable). This can be done with the aid of the product gauge of this invention.

When the third phase is completed, the system is ready for actual product inspection using the refined discriminant function and the first threshold values. In actual product inspection, the system uses the refined discriminant function to compute a processed value for each product image. If the processed value for a product image is between the first threshold values, the product is accepted as having an acceptable appearance. If the processed value for a product image is not between the first threshold values, the product is rejected as having an unacceptable appearance.

The system greatly reduces the level of operator skill and amount of operator time required to set the system up for a product inspection task. This is especially true when the system is used in conjunction with the product gauge invention described herein. The operator is only required to identify a relatively small number of acceptable images (e.g., 25) during the first phase. The product gauge aids the operator in this identification. The initial discriminant function is then computed automatically using a simple and rapid technique such as a logical OR of the small number of first phase images. The entire second phase may also be automatic. And during the third phase, the operator is only required to decide on the acceptability of the relatively small number of images whose processed values fall outside the first threshold values but between the second threshold values. The product gauge can aid the operator in this function as well.

Further features of the invention, its nature and various advantages will be more apparent from the accompanying drawings and the following detailed description of the preferred embodiments.

BRIEF DESCRIPTION OF THE DRAWINGS

FIG. 8 is a histogram diagram useful in explaining certain features of the invention.

FIG. 9 shows several equations which may be employed in accordance with the invention.

FIG. 11a shows a front view, FIG. 11b a side view and FIG. 11c the back view product gauges from three video screens.

DETAILED DESCRIPTION OF THE PREFERRED EMBODIMENTS

Figure 1:
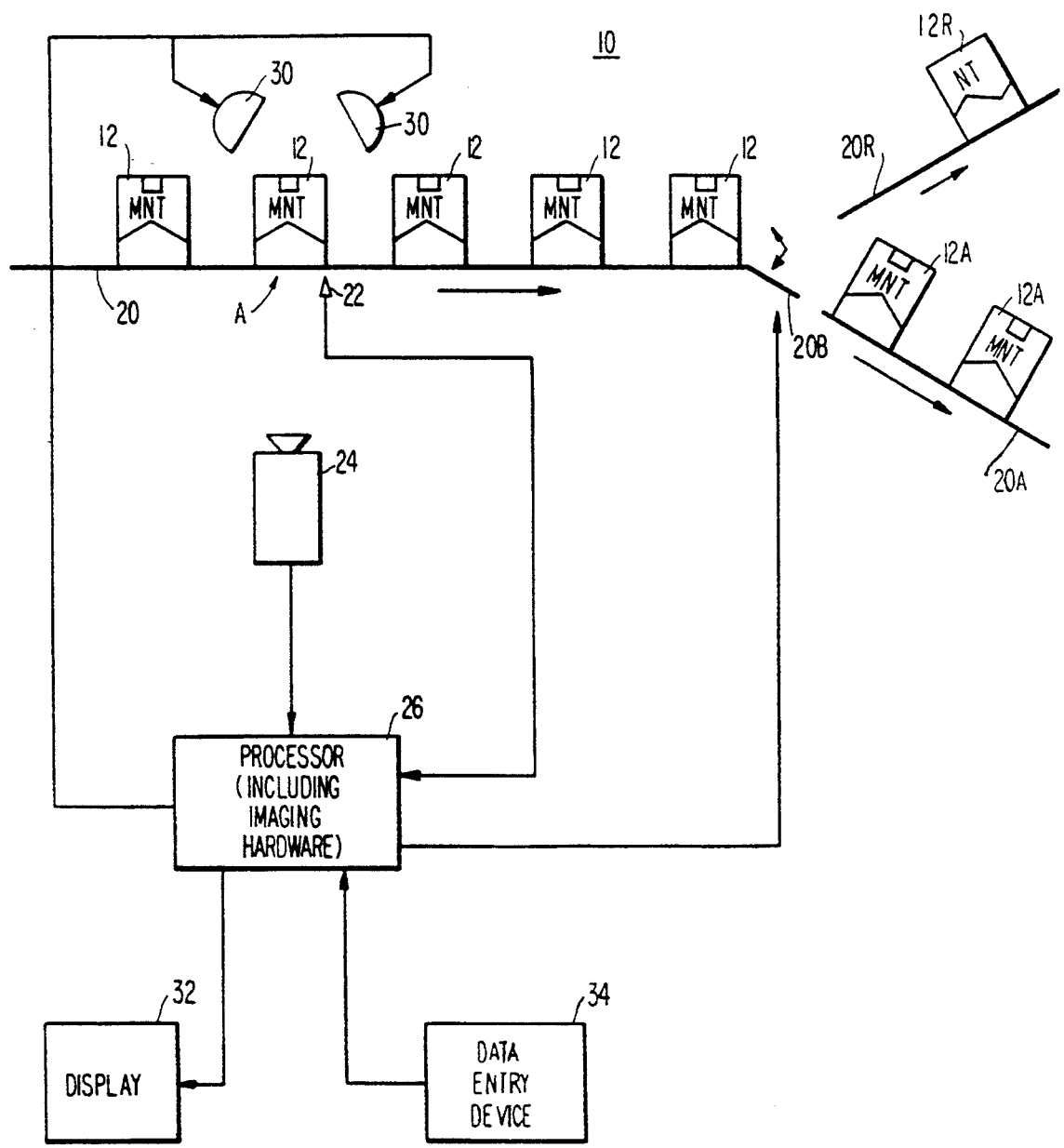
FIG. 1 is a simplified schematic block diagram of an illustrative embodiment of an optical product inspection apparatus constructed in accordance with the principles of this invention.

A product inspection apparatus is used by manufacturers to reject defective products. Examples of such an apparatus can be found in U.S. Pat. Nos. 4,053,056, 4,972,494 and 4,589,140. A typical product inspection apparatus includes a conveyor apparatus for conveying the objects or products to be inspected by optical product inspection means as they come off the production line. The products may be illuminated by a conventional light source to enable cameras and imaging hardware of an optical product inspection means to acquire a two-dimensional image of the product when it passes by. The cameras of these optical product inspection means may be conventional monochrome or polychrome video cameras such as any NTSC or RGB compatible cameras. A number of cameras may be used together to acquire an image of different views or sides of the products to be inspected.

Each two-dimensional image acquired by the imaging hardware of the optical product inspection means is processed by the optical product inspection means to determine whether or not that product has an acceptable image. If the product has an acceptable image, it is directed to a conveyor system for further processing. If the product's image is not acceptable, the product is directed to a different conveyor system for defective products. This whole process can usually be monitored and controlled by an individual via a video screen or monitor. A video monitor is considered equivalent to a video screen herein.

The determination of whether a product has an acceptable image is done electronically by the optical product inspection means.

In the set-up and maintenance of a product inspection apparatus, reference information is entered. This reference information can be entered via a configuration phase or a "training phase" in which one or many ideal or acceptable products are passed through the apparatus and the images or information from their images are stored and processed by the optical product inspection means. Alternatively, an image of a model of an acceptable product or information from that image or other information may be entered directly by electronic means into the optical product inspection means.

After this reference information is entered, the optical product inspection means is applied to the production line. The reference information is compared by the optical product inspection means with information or images from products from the production line to determine whether to accept or reject a product. During the inspection of products, it is usually desirable to monitor the optical product inspection means effectiveness and make changes to adapt the means to new requirements or product changes. In that case, the means should be adaptable and adjustable.

This invention provides a product gauge that may be integrated into a product inspection method or apparatus to improve the performance of the optical product inspection means of that method or apparatus. The product gauge provides alignment and processing improvements to the optical product inspection means and to the users of those means.

The product gauge is comprised of an electronic template. The template is preferably formed from a figure or image on a video screen. The template can have symbols, points, zones, shaded areas or line markings or some combination of these.

One embodiment of the product gauge invention described here is an image-based product gauge. This image-based embodiment includes a template image that is superimposable on a video screen over an image of a product that is to be inspected. The template image can represent a two or a three dimensional view of a product.

Figure 10:
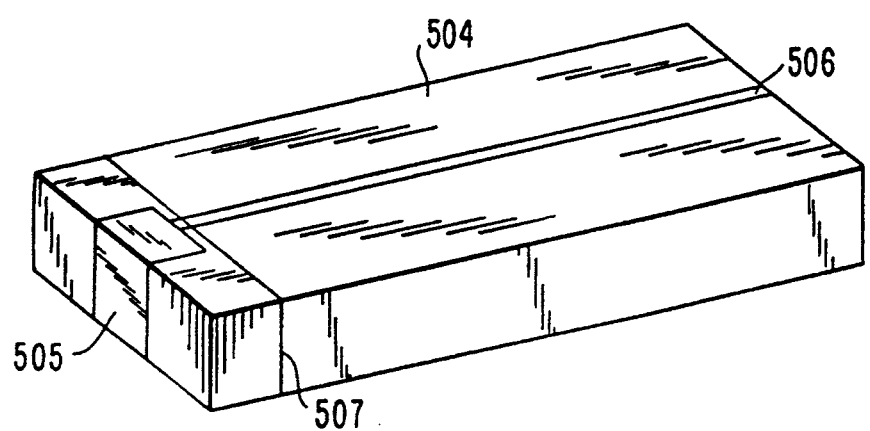
FIG. 10 is a drawing of a model used to create a product gauge.

A physical representation of a package, referred to here as a model, is preferably used as the basis for the creation of the image-based product gauge embodiment. The model can consist of a template surface, with symbols, points, zones, shaded areas or line markings with a wood, metal, plastic or other suitable material frame (FIG. 10). An ideal or an acceptable package can also be used for the model used as the basis of the image-based product gauge. Regardless of the particular construction of this model, the model of the package should resemble the product to be inspected both dimensionally and be of the same weight. Regardless of what model is used, it is the image on the video monitor of that model which forms the template image of the product gauge.

Another embodiment of the product gauge described here is electronically constructed. Like the image-based product gauge embodiment, this electronically constructed embodiment utilizes a template image that is superimposable on a video screen over a product to be inspected. This product gauge template image can also represent a two or a three dimensional view of a product.

For the electronically constructed embodiment, a line-drawing computer program can be used to create a line-drawing of a product gauge on a video screen component of the optical product inspection means. The operator can trace the image of a model, similar to the model described above for the image-based embodiment, to create the electronically drawn product gauge. The line-drawing can result in symbols, points, zones, shaded areas or line markings or some combination of these. Thus, while the electronically constructed product gauge can be "based" on a product or model like the image-based product gauge, the electronically constructed product gauge can differ because of the line-drawing. The line-drawing forms the template image of the product gauge.

The electronically constructed product gauge can also be constructed using other methods. Instead of a line-drawing computer program, certain data points can be directly entered by an operator. The data points can also be generated electronically. These data points can be selected to correspond to important features of a product such as an edge or an artwork area. In this embodiment, the data points are then used to form the product gauge or form the product gauge's basis.

Regardless of the particular construction of the electronically constructed product gauge, an image of the products to be inspected as they pass by the apparatus coexists on the video screen with a superimposed image of the product gauge.

The electronically constructed product gauge is constructed, and the image-based product gauge is created on the video screen under static conditions. In a preferred embodiment, the product gauge can be altered or changed to account for translational movements or other changes in the product inspection apparatus under dynamic conditions.

The electronically constructed product gauge, although more complex than the image-based product gauge, solves some of the problems experienced with the image-based product gauge. Fouling or scratching of the model or a disturbed or fuzzy image on the video screen of the model that is used for the image-based product gauge can create difficulties that are not present when the product gauge is electronically constructed.

The image-based, the electronically constructed and other embodiments of the product gauge of this invention are constructed with the same uses and specifications in mind.

The product gauge of this invention can be used to aid in the alignment the optical product inspection means and other components of the product inspection apparatus. This greatly simplifies set-up and operation of any product inspection apparatus. The operator takes the product gauge template, an image on a video screen, and superimposes it over the image of a product from the inspection line. The product gauge and the product to be inspected should be aligned. If they are not, either one or both can be aligned or adjusted. Since all areas or sides or just some of the areas or sides of the product may be inspected, product gauges should be constructed to be able to correctly align the components of the product inspection apparatus with all of the areas or sides of the product that are to be inspected so that the inspection can occur. The placement of the product on the conveyor systems, the lighting, the camera or cameras and other components can all be aligned and adjusted by reference to the product gauge. This alignment can be monitored by the operator on a video screen component of the optical product inspection means by comparing the image of the product gauge with the image of the product to be inspected.

In the one embodiment, the product gauge image appears on the video screen, either as lines, points, symbols, zones, or shaded areas or some combination of these. This product gauge image should correspond on the video screen to where the image of the products on the production line is on the video screen. Otherwise, the various components of the apparatus are brought into alignment so that the product gauge, the products, and other components of the optical product inspection means correspond. The product gauge itself can also be adjusted, in one embodiment, to be aligned with the image of the products as they pass by on the video screen.

In one embodiment of the product gauge, if the product gauge represented on the screen is not aligned with the products from the production line, the optical inspection means and/or the product conveyor system can be adjusted, by electronic feedback or other appropriate mechanisms, to come back into alignment.

The product gauge is also constructed to achieve other results. The placement of the symbols, points, zones, shaded areas or lines or some combination of these on these embodiments of the product gauge are tailored according to the specific product that is being inspected. Important areas for alignment purposes such as edges or artwork areas can be delineated. This delineation on the product gauge can be of the important areas or zones on the product and thereby help the individual monitoring the production inspection apparatus concentrate on key areas. The product gauge can thus be used to highlight problem areas of products for the individuals monitoring the apparatus. Important features of a package or product such as artwork or the positioning of functional features such as tabs, foils or seams can also be inspected with greater precision and accuracy.

In one embodiment, the product gauge of this invention aids the individual monitoring the apparatus in the "teaching phase" or set-up of the apparatus. As products pass by, the individual monitoring the apparatus with the aid of the product gauge can select acceptable or rejectable products and enter this selection into the optical product inspection means. The product gauge focusses or concentrates the individual monitoring the apparatus on the features of acceptable or rejectable products. For example, if in the image of a product shows that a feature of one product appears to fall outside the feature as delineated by the product gauge, the operator can reject that product as defective. This human selection of acceptable/rejectable products may form the basis for the optical product inspection means making its determination of whether to reject a product after this initial "teaching phase" or set-up is completed.

For another example, if the products to be inspected contain labels on their surface, line markings on the template of the product gauge can be made to correspond with the correct positioning of the labels. By superimposing the product gauge over the products, the operator can determine whether the labels are in the correct position by comparing line markings on the product gauge's template with the labels on the product to be inspected. Products that have labels that fall outside of the markings on the product gauge can be correctly rejected.

This human selection of acceptable/rejectable products aided by the product gauge can also be used to update the determination basis of acceptable/rejectable of the optical product inspection means as it is operating under dynamic conditions.

The delineation of certain areas by the product gauge of this invention can enable the optical product inspection means to electronically identify certain areas of the image of a product to be inspected. Once that means electronically identifies an area, it can electronically analyze that area in detail. Potential defect locations can be focussed or concentrated on.

In another embodiment of the product gauge of this invention, when a product is rejected by the product inspection apparatus, the area of the product that was found to be defective can be highlighted on the image of the product gauge that is on the video screen. This aids in identifying why products are rejected and in troubleshooting the optical product inspection means.

The product gauge of this invention enhances the universality of the product inspection apparatus. If the apparatus and the optical product inspection means component are designed to generally work with many products, they can be designed to be integrated with specific product gauges that perform the function of tailoring an apparatus to a specific product. The product gauge can be used to quickly and accurately tailor a generalized product inspection apparatus to a specific product. Thus, the product gauge can enable the optical inspection means to quickly change from inspecting one product to inspecting another product.

The product gauge can also be used to ensure consistency between two or more independent optical product inspection means. If two or more independent optical product inspection means are inspecting the same products from separate production units at the same production site or even at different production sites, a problem in consistency or standardization can occur between the separate optical product inspection means. The same product gauge, used with all of the optical product inspection means that are inspecting the same product, can provide consistency and standardization in the inspection. The product gauge can be transported or transferred from one optical product inspection means to another electronically.

The product gauge also helps with the set-up of the optical product inspection means' ability to detect defective products. If so construed, the range and specification of dimensional and quality parameters of the product to be inspected can be initially set in the optical product inspection means by "scanning" a product gauge. Then a "teaching phase" or information can be entered, based on the dimensional and quality parameters of the product gauge, in order to set the standards for acceptance. Finally, after the dimensional and quality parameters are set with the product gauge, and after the standards for acceptance are electronically set, the system can be applied to a production line.

The product gauge of this invention can be constructed to work with many different product inspection apparatuses that may include optical product inspection means. One such optical product inspection means, the optical inspection system of U.S. application Ser. No. 661,809, will now be described in detail. The image-based or the electronically constructed embodiments of the product gauge as well as other embodiments similar to those discussed herein can all be used with this system.

As shown in FIG. 1, a typical product inspection system 10 constructed in accordance with this invention includes conveyor apparatus 20 for conveying the objects or products 12 to be inspected, one after another, from left to right as viewed in the FIG. Each time conventional product sensor 22 detects a product 12 at a predetermined location A opposite conventional camera 24, conventional processor 26 (which includes conventional imaging hardware) causes conventional light sources 30 to briefly illuminate the product, thereby allowing camera 24 to capture what is effectively a still image of the product. This still image is fed to processor 26 which digitizes and further processes the image. Processor 26 is augmented by conventional video display 32 and conventional data entry device 34 (e.g., a keyboard, mouse, and/or touch screen elements associated with display 32). Processor 26 can cause display 32 to display a product image captured by camera 24, and can augment that display with other information such as the outline of an acceptable product image and/or outlines of certain features of an acceptable product image. This could include the product gauge as described herein. The operator may use this augmenting information to help determine whether the product image being displayed is acceptable. The operator may use data entry device 34 to control the overall operation of the system, as well as to respond to inquiries from the system (e.g., as to whether or not the operator judges the product image currently shown on display 32 to be acceptable).

The system may be set up to perform a product inspection by operating it substantially as though it were inspecting products, i.e., by using conveyor 20 to convey representative products one after another past camera 24 and by using the other elements of the system to process the images of those products as described in detail below. During actual product inspection, processor 26 determines whether the image of each successive product 12 is acceptable, and when that product reaches a controllable branch 20B in conveyor 20, processor 26 controls that branch so that acceptable products 12A are directed to accepted product conveyor 20A, while unacceptable products 12R are directed to rejected product conveyor 20R.

While FIG. 1 suggests that system 10 operates on a single elevational image of products 12, it will be apparent to those skilled in the art that the system could be set up to test multiple images of the products taken from different angles and including perspective views so that as many surfaces of the objects are inspected as are desired. Similarly, although the system will be explained in terms of monochrome (e.g., black and white) images, it will be apparent to those skilled in the art how the system can be modified to inspect in full color. Thus camera 24 may be a conventional NTSC or RGB compatible camera. Processor 26 may be a suitably programmed conventional 386 personal computer workstation such as a CAT386 workstation available from Comark Corp. of Medfield, Mass. with a conventional IM-1280 imaging hardware system available from MATROX Electronic Systems Limited of Dorval, Quebec, Canada.

Figure 2A:
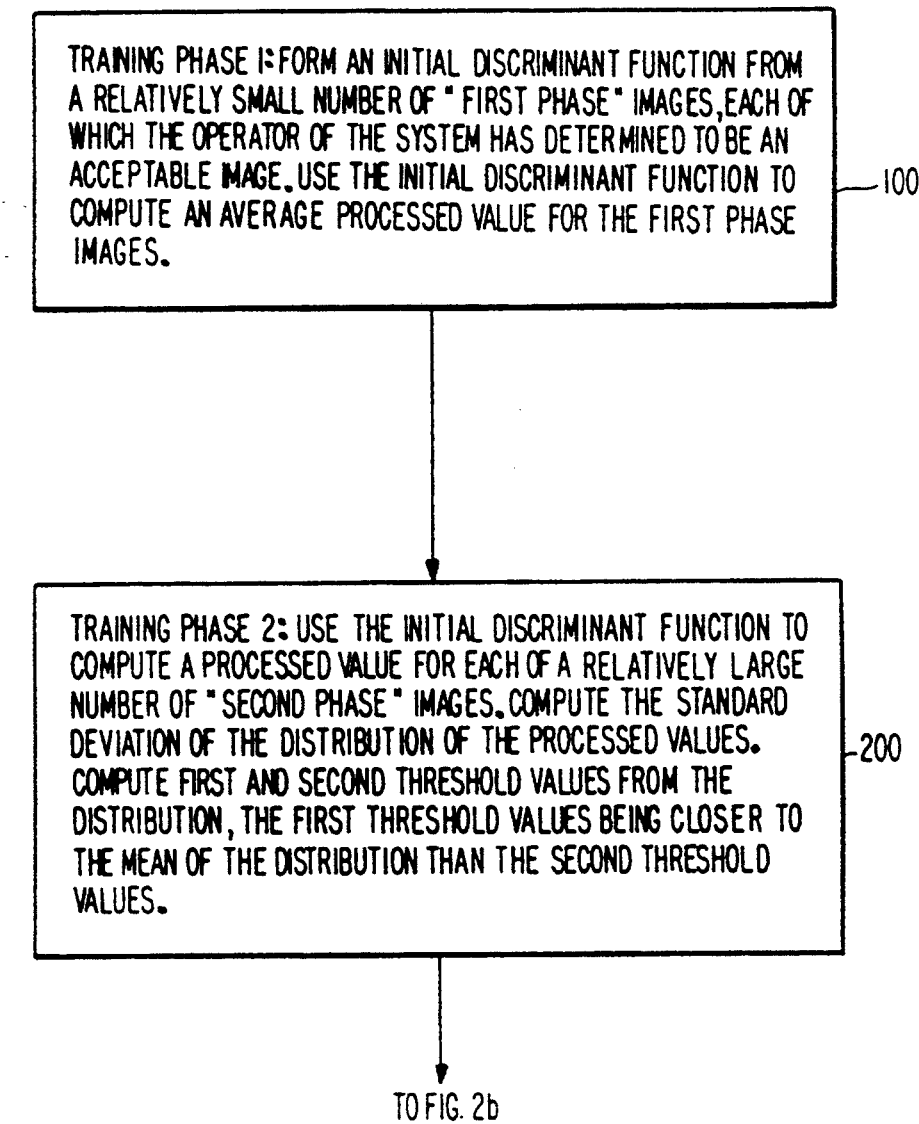
FIGS. 2a and 2b (referred to collectively as FIG. 2) are a flow chart of an illustrative optical product inspection method in accordance with this invention.
Figure 2B:
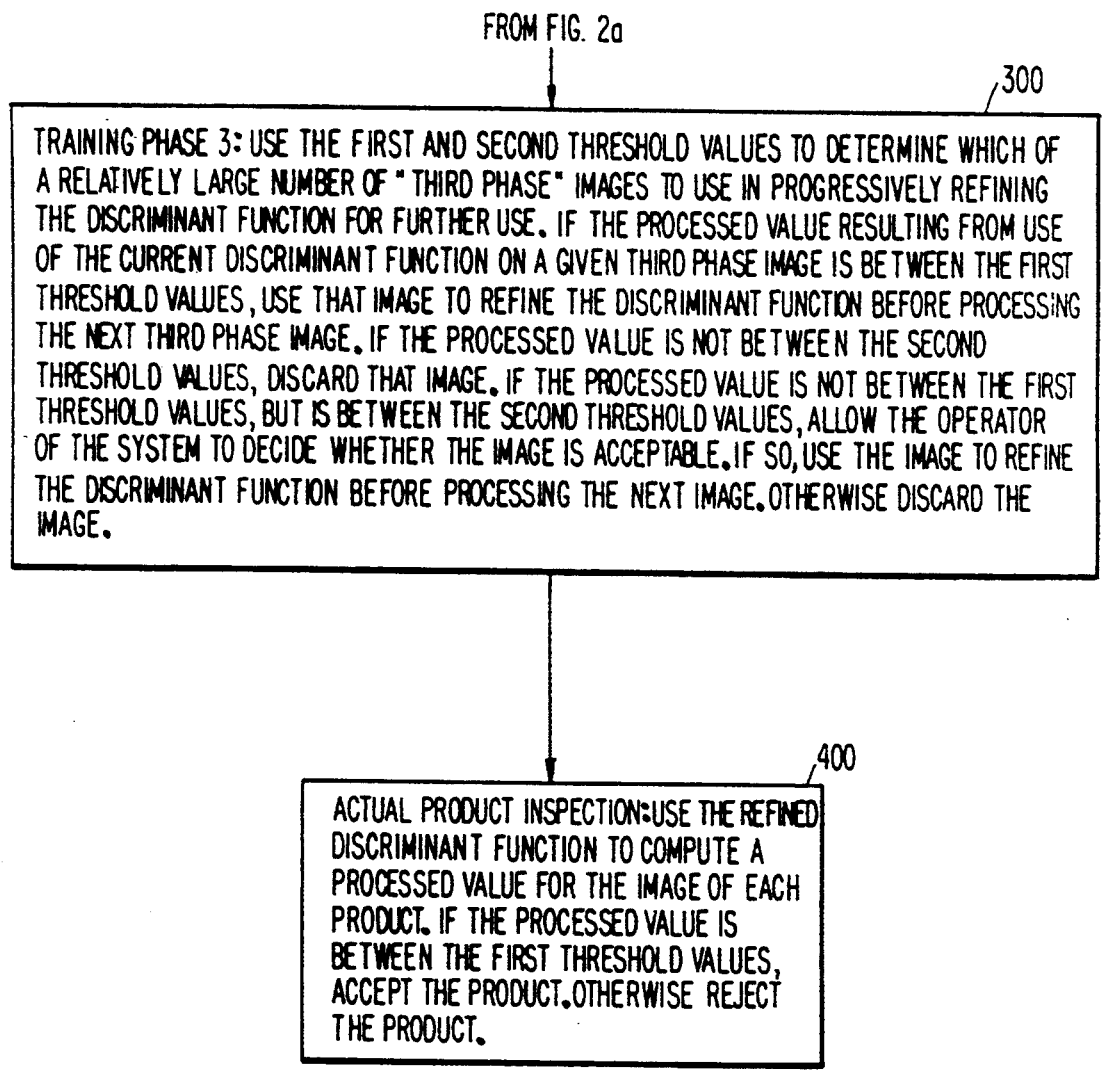

An overview of a preferred embodiment of the method of this invention is shown in FIG. 2. Basically the depicted embodiment comprises a training portion, including three successive phases 1, 2, and 3 (shown in boxes 100, 200, and 300, respectively), and actual product inspection (shown in box 400). During the three training phases, the system "learns", by appropriately processing product images with appropriate but relatively limited input from the human operator of the system, how to discriminate between good and bad images. The product gauge as described herein is used to aid the human operator in these functions. Thereafter, during actual product inspection, the system uses this "knowledge" to accept or reject products.

Figure 3A:
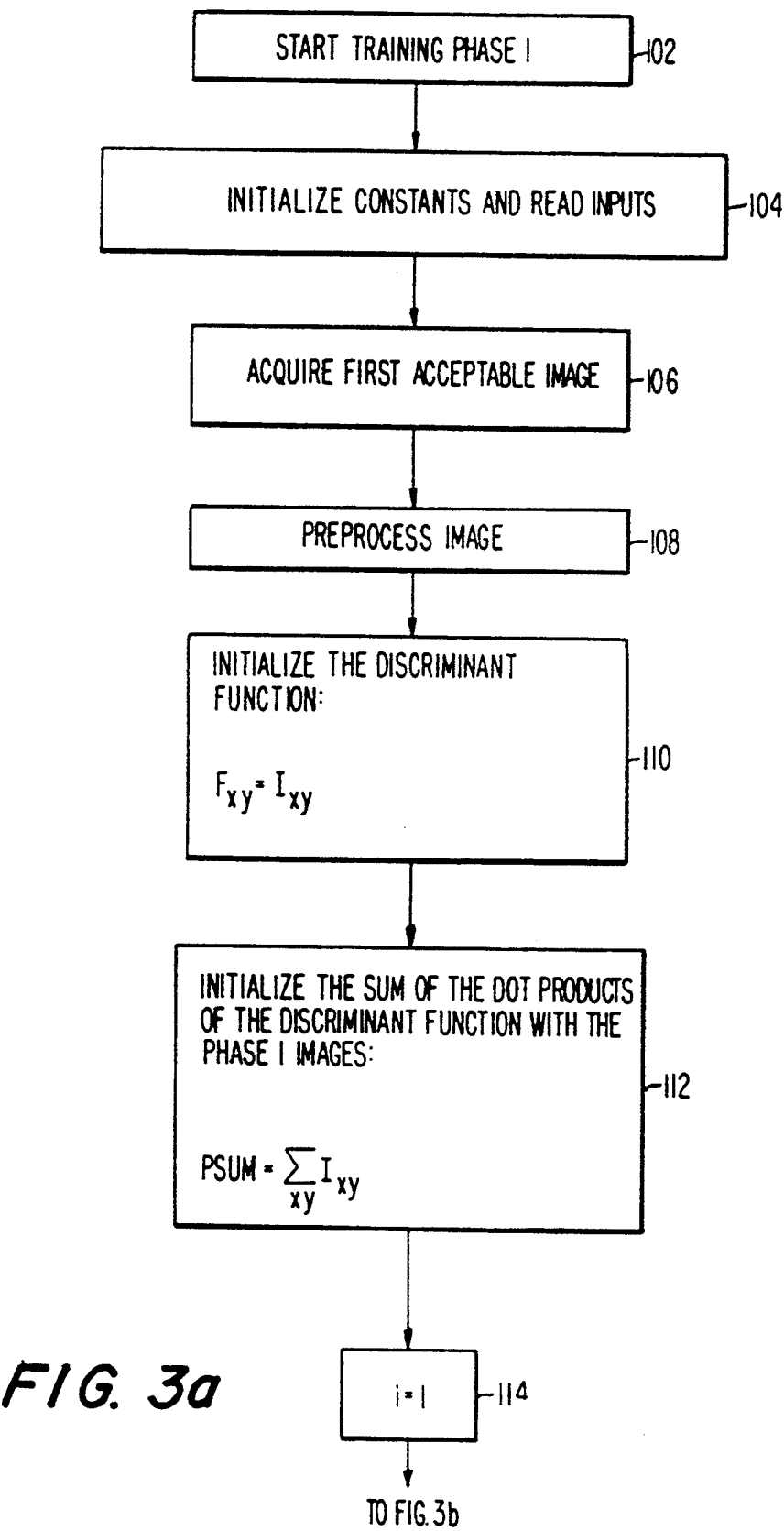
FIGS. 3a-3c (referred to collectively as FIG. 3) are a flow chart of an illustrative, more detailed embodiment of one of the steps shown in FIG. 2.
Figure 3B:
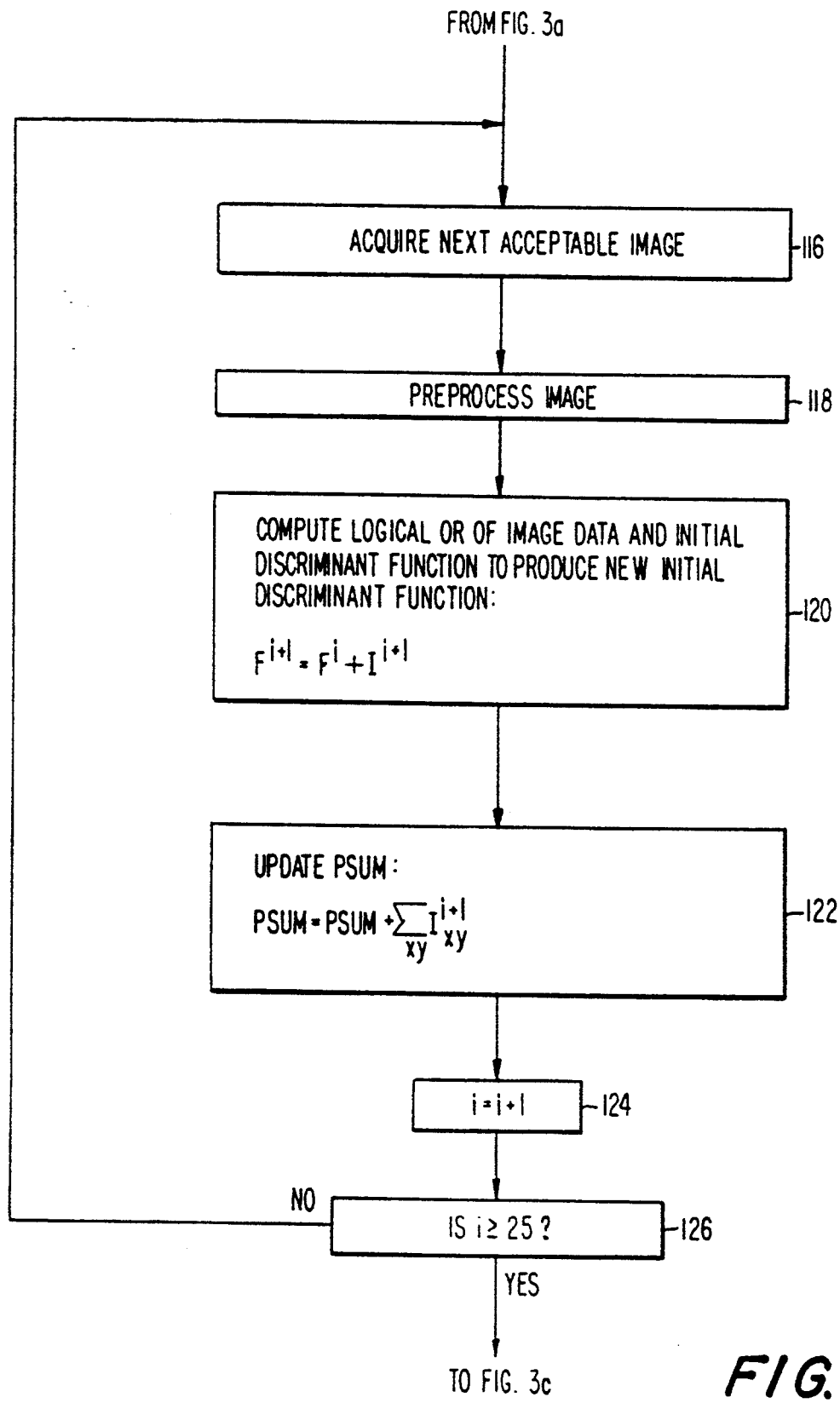
Figure 3C:
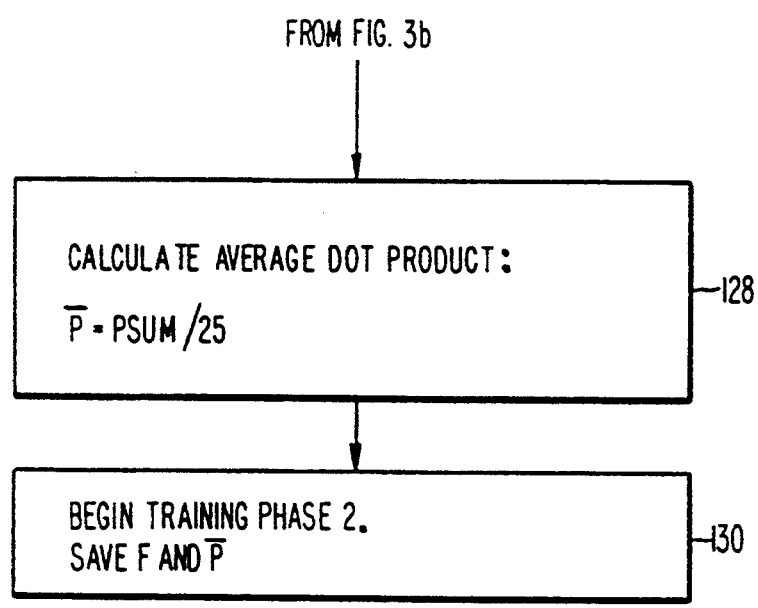

In training phase 1 (step 100 in FIG. 2) an initial discriminant function F (which may be thought of as a two-dimensional matrix commensurate with the two-dimensional data for the product images or product image portions to be inspected) is formed from the data I for a relatively small number of "first phase" images. Although this initial discriminant function could be computed in many other ways in accordance with this invention, in the preferred embodiment (shown in detail in FIG. 3) a relatively simple technique (i.e., a logical OR of the phase 1 images) is used in order to allow a relatively small and inexpensive processor 26 to perform the necessary calculations without requiring more time than the operator of the system needs to provide the necessary inputs regarding each successive first phase image. Accordingly, as shown in FIG. 3 training phase 1 starts with step 102, and in step 104 various program constants are initialized and inputs are read (e.g., from the memory which is part of processor 26 and/or from data entry device 34). For example, step 104 may include selection of an image outline overlay to be displayed with product images on display 32 to help the operator judge the acceptability of images. Step 104 may also include the product gauge of this invention. Step 104 may also include selection of the boundaries of the portion or portions of the image to be processed. As another example, step 104 may include selection of a threshold to be used in binarizing the image data as discussed below. Any other necessary system initialization tasks may be performed as part of step 104.

In step 106 the system acquires the data for the first of the first phase images. This is done by having camera 24 capture a product image as described above. Processor 26 then digitizes this image in full gray scale and causes display 32 to display this gray scale image with any augmenting information (such as an outline overlay or product gauge) selected in step 104. The operator, with the aid of a product gauge as described herein, then indicates (via data entry device 34) whether or not the displayed image is acceptable. If so, control passes to step 108. If not, step 106 is repeated with new product images until an image acceptable to the operator is found.

In step 108 the first acceptable image is preprocessed. This preferably includes edge detecting the gray scale image so that pixels at or near significant changes in image brightness are emphasized (e.g., increased in value) relative to other pixels which are de-emphasized (e.g., decreased in value). Edge detection is a well-known technique which is discussed in more detail, for example, in U.S. patent application Ser. No. 308,739, filed Feb. 9, 1989 and hereby incorporated by reference herein. After edge detection, the edge detected image is preferably binarized so that all pixels having values on one side of a predetermined binarization threshold level (which may have been selected in step 104) are assigned one binary value (e.g., 1), while all pixels having values on the other side of the binarization threshold level are assigned the other binary value (e.g., 0).

In step 110 the initial discriminant function F is set equal to the first acceptable image data from step 108.

In step 112 the sum of the dot products of the discriminant function and the phase 1 image data is initialized. Because at this point F and I are the same, the initial dot product of F and I is just the sum of the pixel values of I.

In step 114 an index value i is set equal to 1.

In step 116 the system acquires the next acceptable image. Step 116 is therefore an exact repetition of above-described step 106.

In step 118 the data for the next acceptable image (acquired in step 116) is preprocessed exactly as described above in connection with step 108.

In step 120 the initial discriminant function is updated with the new image data by computing the logical OR of the new image data and the old initial discriminant function data to produce a new initial discriminant function. In other words, for each pixel location in which either or both of the image data and the old initial discriminant function data are 1, the new initial discriminant data value is 1, while for each pixel location in which both the image data and the old initial discriminant data are 0, the new initial discriminant function data value is 0.

In step 122 the sum of the dot products of the discriminant function and the phase 1 image data is updated for the current image. Because the 1-valued pixel locations in each image are always a subset of the 1-valued pixel locations in F, each new dot product is just the sum of the pixel values in the current image I.

In step 124 the index i is incremented by 1, and in step 126 the new value of i is tested to determine whether it is greater than or equal to 25. This is an arbitrary number which determines how many first phase images will be used to compute the initial discriminant function. Although any other number could be used, 25 has been found to give good results. If i has not yet reached 25, control returns to step 116 and steps 116-126 are repeated until the test in step 126 is satisfied and control consequently passes to step 128.

In step 128 the average of the dot products of F and each of the first phase images is computed by dividing PSUM by 25 (the number of first phase images).

In step 130 training phase 2 (step 200 in FIG. 5) begins. The initial discriminant function F from the last performance of step 120 and the average dot product are saved.

Figure 4A:
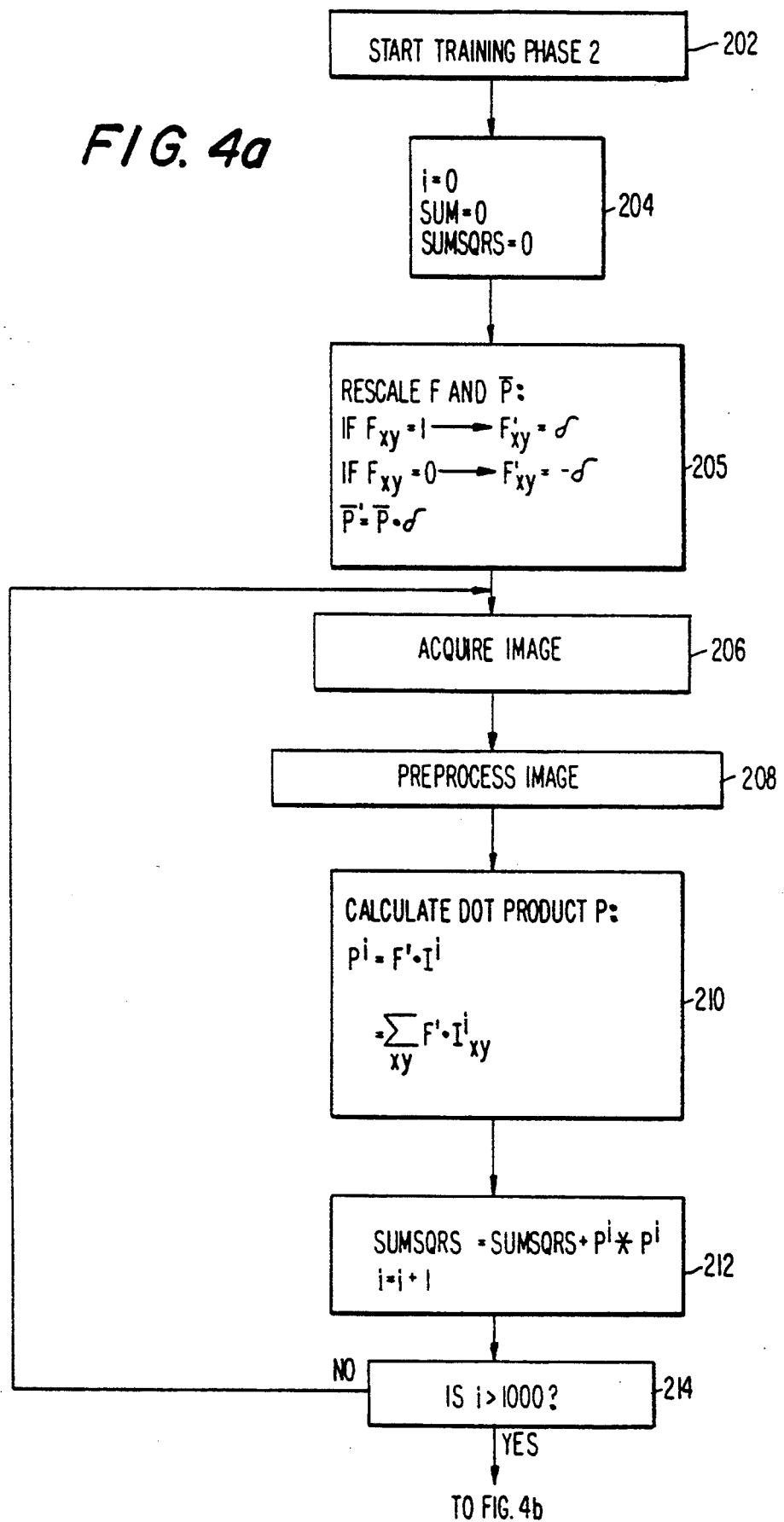
FIGS. 4a and 4b (referred to collectively as FIG. 4) are a flow chart of an illustrative, more detailed embodiment of another one of the steps shown in FIG. 2.
Figure 4B:
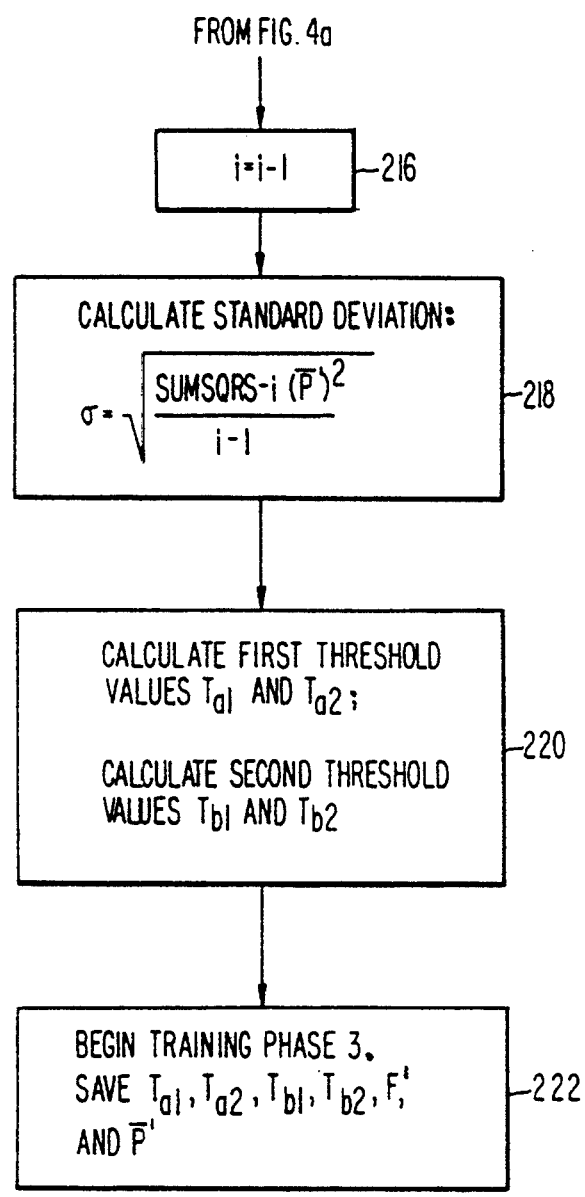

In step 200 the initial discriminant function F is used to compute statistical information about the images being processed. Again, although this can be done in other ways in accordance with this invention, a preferred embodiment of step 200 is shown in FIG. 4 and will now be described by way of illustration.

Training phase 2 starts in step 202. In step 204 index value i is set equal to 1, variable SUM is set equal to 0, and variable SUMSQRS (for sum of squares) is also set equal to 0.

In step 205 the initial binary discriminant function F is converted to bipolar form using initial positive and negative values such that the final discriminant function values take advantage of the full arithmetic range of processor 26. To reflect this in the average dot product, the average dot product is also scaled by the same scale factor in step 205. For example, if processor 26 performs 8-bit arithmetic with values between $-128$ and $+127$, the initial values now used in function F may be $-50$ (for pixel locations where the F value was formerly 0) and $+50$ (for pixel values where the F value was formerly 1), and the average dot product from step 128 may be multiplied by 50.

In step 206 a product image is acquired in a manner similar to above-described step 106, except that during training phase 2 the operator of the system is not required to determine whether the image is acceptable. Accordingly, all the images received during phase 2 are used. These images can therefore be expected to exhibit the normal range of variation for the product images that the system will subsequently encounter during actual product inspection. In addition, because no interaction with the operator of the system is required during this phase, the phase 2 images can be processed much faster (e.g., at actual product inspection rates) than the phase 1 images.

In step 208 the image data acquired in step 206 is preprocessed exactly as described above in connection with step 108.

In step 210 the dot product P of the rescaled initial discriminant function F from step 205 and the image data I from step 208 is calculated. This calculation involves multiplying the value of F at each pixel location by the value of I at that pixel location, and then summing all of the resulting products to produce the dot product P. Elsewhere in this specification the more generic term "processed value" is sometimes used for the dot product P. It will be noted that if I is identical to F, P will be a certain number, but if I differs from F at certain pixel locations, P will be greater or less than that number. The amount by which P differs from that number is a measure of how much I differs from F. In practice, the values of P will typically exhibit an approximately normal (i.e., approximately Gaussian) distribution about some mean or average value.

In step 212 the variable SUMSQRS is incremented by the square of the value of P from step 210, and the index value i is incremented by 1.

In step 214 the index value i is compared to an arbitrary number (e.g., 1000) which is the predetermined number of images to be processed in phase 2. Although any sufficiently large number of images can be processed in phase 2, 1000 images have been found to give good results. If the test in step 214 is not satisfied, control returns to step 206 where processing of the next phase 2 image begins. When 1000 phase 2 images have been processed as described above, the test in step 214 is satisfied and control passes from step 214 to step 216.

In step 216 the index value i is reduced by 1 to reverse the last incrementing of that value.

In step 218 the rescaled average dot product from step 205 and the value of the SUMSQRS variable are used to compute the standard deviation of the previously computed dot products.

Figure 7:
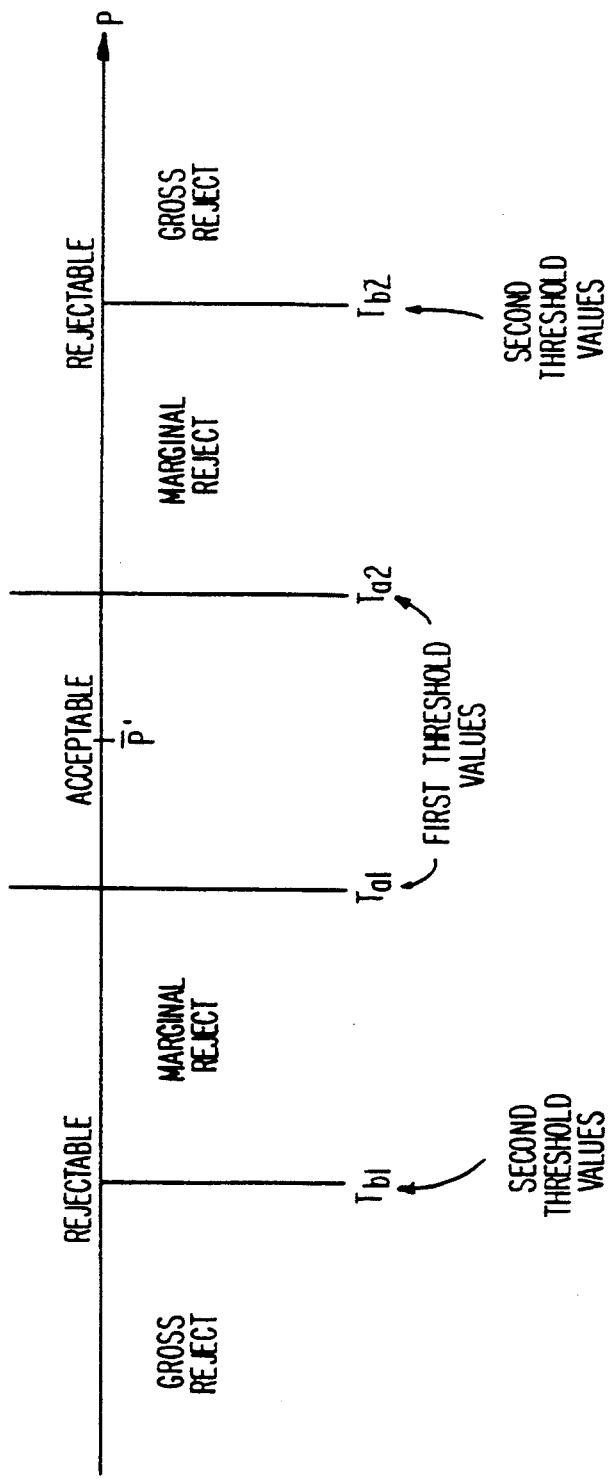
FIG. 7 is a diagram of a dot product spectrum which is useful in explaining certain features of the invention.

In step 220 two first threshold values and two second threshold values are selected so that the distribution of phase 2 dot products is subdivided by these threshold values as shown in FIG. 7. For example, the first threshold values may be chosen so that a fraction f1 of the dot products are greater than the upper one of these threshold values and the same fraction of dot products are less than the lower one of these threshold values. The fraction f1 is preferably significantly greater than one-half the fraction of images which are expected to be defective in order to minimize the possibility that any unacceptable images have dot products that are greater than the upper or less than the lower of these first threshold values. Images with dot products between the first threshold values are therefore automatically acceptable as indicated in FIG. 7.

The second threshold values are chosen so that a smaller fraction f2 of the dot products are greater than the upper one of these threshold values and the same smaller fraction of dot products are less than the lower one of these threshold values. The fraction f2 is preferably significantly smaller than one-half the fraction of images which are expected to be defective in order to minimize the possibility that any acceptable images have dot products that are less than the lower or greater than the upper one of these second threshold values. Images with dot products outside the region bounded by the second threshold values are therefore automatically rejectable as "gross rejects" as indicated in FIG. 7. Images with dot products outside the region bounded by the first threshold values but inside the region bounded by the second threshold values are "marginal rejects" as indicated in FIG. 7. Operator intervention is required to determine whether such an image should be accepted or rejected. The product gauge of this invention can aid the operator in this determination.

It may be convenient and appropriate to choose the threshold values described above assuming the distribution of dot products to be Gaussian as shown, for example, in FIG. 8, and therefore characterized by a standard deviation (given by the equation in step 218). In that case, the thresholds can be defined by the equations shown in FIG. 9. The average dot product used in these equations is the rescaled average dot product from step 205. The alpha coefficients used in these equations with the standard deviation are selected so as to achieve the target fractions f1 and f2 for a Gaussian distribution. These values can be readily selected with the aid of available tables of the properties of the Gaussian distribution. The most preferred approach is to select the first threshold values without assuming a Gaussian distribution (i.e., as described prior to the above discussion of the Gaussian distribution), and to use the second method (i.e., the Gaussian distribution assumption) to select the second threshold values. Note that in FIG. 8 the region A corresponds to the "acceptable" region of FIG. 7, the regions B correspond to the "gross reject" regions of FIG. 7, and the regions C correspond to the "marginal reject" regions of FIG. 7. Thus region A includes dot products known to be associated with clearly acceptable images, whereas regions B include dot products known to be associated with clearly unacceptable images. Regions C are those along the distribution of dot products P which may be marginally acceptable. Adaptive training is performed in phase 3 as discussed below with respect to dot products lying in region A, and also with respect to dot products lying in regions C which the operator of the system determines to be acceptable.

After the second threshold values are calculated in step 220, control passes to step 222 to begin training phase 3 (step 300 in FIG. 2). The first and second threshold values from step 220 are saved, as are F and the rescaled average dot product from step 205.

In training phase 3 (step 300 in FIG. 2) the statistical information from phase 2 is used with the image data from another statistically significant number of images to refine the initial discriminant function F. Again, although this can be done in other ways in accordance with this invention, a preferred embodiment of training phase 3 is shown in FIG. 5 which will now be described by way of illustration.

Figure 5A:
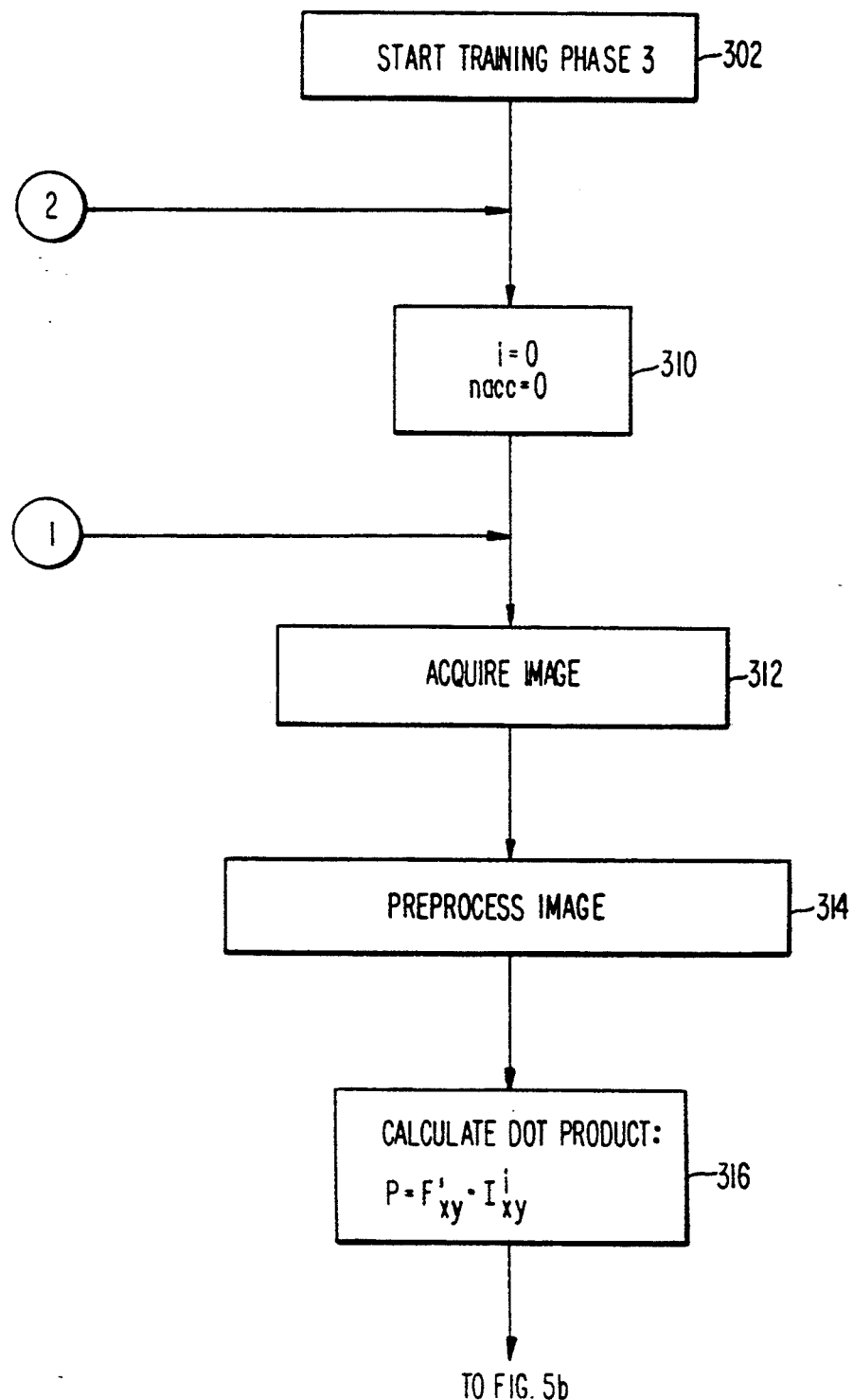
FIGS. 5a-5c (referred to collectively as FIG. 5) are a flow chart of an illustrative, more detailed embodiment of still another one of the steps shown in FIG. 2.
Figure 5B:
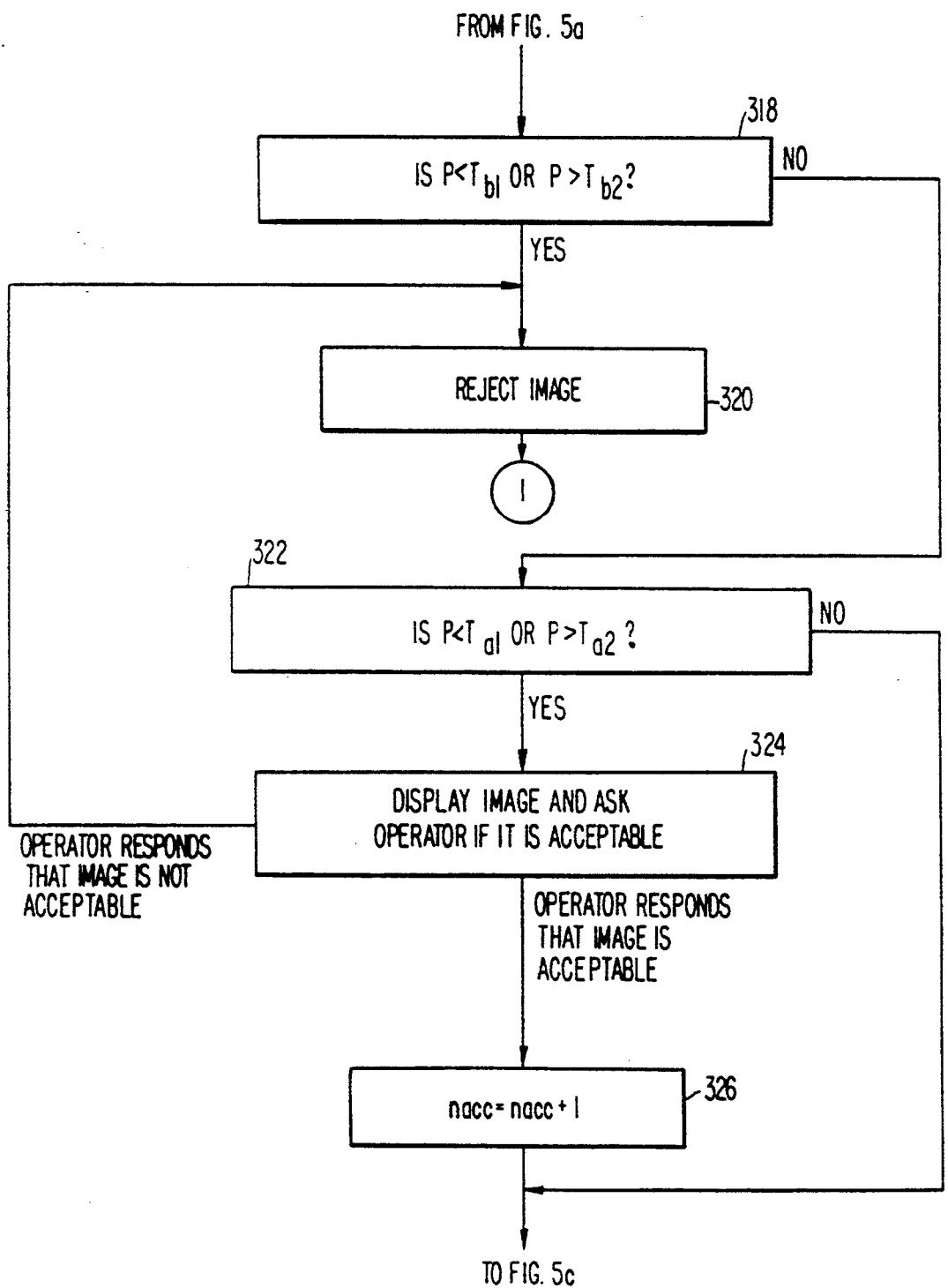
Figure 5C:
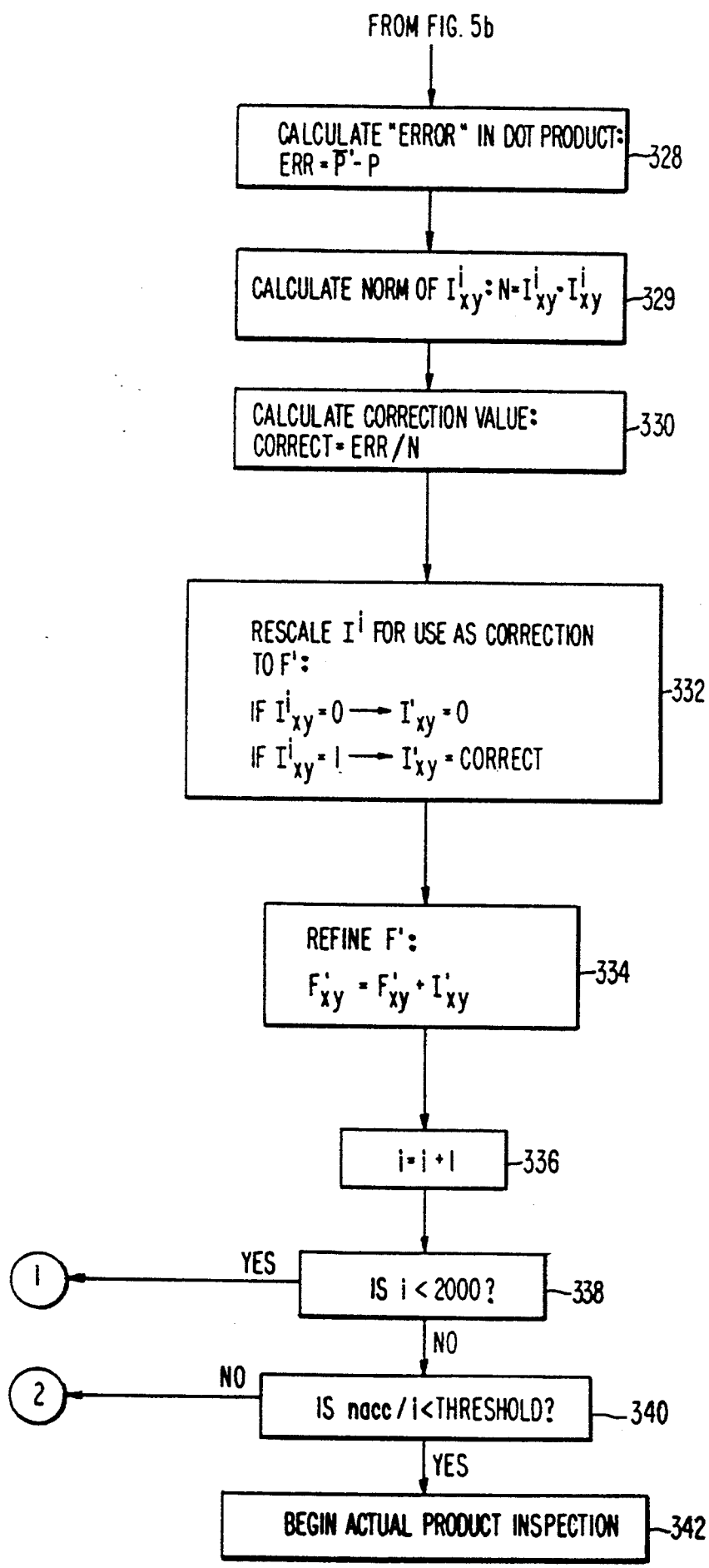

As shown in FIG. 5, training phase 3 begins in step 302, and in step 310 an index value i is initialized to 0, and a counter - used during phase 3 to count the number of marginally acceptable images which the operator of the system decides to accept is also initialized to 0.

In step 312 a phase 3 image is acquired exactly as described above in connection with step 206, and in step 314 the data for this image is preprocessed as described above in connection with step 208.

In step 316 the dot product P of the discriminant function and the image data from step 314 is calculated.

In step 318 the dot product value P from step 316 is compared to the second threshold values from step 220. If P is outside the range bounded by these second threshold values, control passes to step 320 where the image is rejected and control is then returned to step 312 to begin the acquisition and processing of the next phase 3 image. On the other hand, if P is in the range bounded by the second threshold values, control passes from step 318 to step 322.

In step 322 the value of P from step 316 is compared to the first threshold values from step 220. If P is outside the range bounded by these first threshold values, control passes to step 324. Step 324 is reached whenever the image is neither automatically rejectable as unacceptable (because the associated dot product is outside the limits defined by the second threshold values), nor automatically acceptable (because the associated dot product is inside the limits defined by the first threshold values). Accordingly, in step 324 the operator of the system is asked to intervene and decide whether or not the image is acceptable. The product gauge as described herein can aid the operator in this determination. The image is displayed on display 32 (as in connection with step 106 above). If the operator responds (again as in connection with step 106) that the image is unacceptable, control passes to step 320 where the image is rejected, and thereafter processing of the next phase 3 image begins as described above. On the other hand, if the operator responds that the image is acceptable, control passes from step 324 to step 326 where the counter nacc is incremented. Thereafter, control passes to step 328. Returning to the other branch from step 322, if P is not outside the limits defined by the first threshold values, the image is automatically acceptable and control passes directly from step 322 to step 328.

Step 328 is performed only when the current third phase image has been determined to be an acceptable image. In most cases the system will have made this determination automatically because the dot product P for the image is between the first threshold values and the image is therefore obviously acceptable. In a few cases, however, the operator will have been required to assist with this determination as described above in connection with step 324. Accordingly, for the most part the processing of images can proceed as rapidly during phase 3 as during phase 2. Only rarely will the operator be required to intervene as a result of the performance of step 324. Moreover, operator intervention should be required even less frequently as phase 3 proceeds and the discriminant function is progressively refined as will now be described.

Step 328 begins the process of refining the rescaled discriminant function using the data from the image which has just been determined to be acceptable. This discriminant function refining process is repeated for each acceptable phase 3 image. In step 328 an "error" value equal to the difference between the average P value from step 205 and P from step 316 is calculated. In step 329 a value N equal to the number of pixels which are "on" in the image data is calculated. In step 330 a correction value equal to the error value from step 328 divided by the value of N from step 329 is calculated. In step 332 the binary image data for the current phase 3 image is rescaled using the correction value from step 330. In particular, each pixel value of 1 is changed to the correction value, while each pixel value of 0 is unaltered.

In step 334 the rescaled discriminant function is refined by incrementing each pixel value by the value associated with that pixel in the rescaled image data from step 332. Step 334 is an "adaptive training" step analogous to the Widrow-Hoff training algorithm sometimes used in signal processing (see, for example, B. Widrow and S. D. Stearns, *Adaptive Signal Processing*, Prentice-Hall, Englewood Cliffs, 1985). Accordingly, as step 334 is performed for successive acceptable third phase images, the rescaled discriminant function becomes better and better at producing dot products (as in step 316) which are clearly differentiated between those associated with acceptable images (P within the range bounded by the first threshold values) and those associated with unacceptable images (P outside the range bounded by the second threshold values). Accordingly, as phase 3 progresses, there should be less and less need to perform step 324, and the amount of input required from the operator of the system should decrease.

In step 336 the index value i is incremented. In step 338 this index value is compared to a phase 3 cut-off value (e.g., 2000 acceptable phase 3 images). If the index value is less than the cut-off value, control passes from step 338 to step 312 where processing of the next phase 3 image begins. As soon as step 338 detects that the index value has reached the cut-off value, control passes from step 338 to step 340.

In step 340 the ratio of the counter value nacc to the index value i is compared to a predetermined threshold value. If this ratio exceeds the threshold value, the system is still tentatively rejecting too many images which the operator of the system has found acceptable in step 324. This indicates that the discriminant function F' is still in need of further refinement. Accordingly, control passes from step 340 to step 310 where the processing of another series of phase 3 images begins again. On the other hand, if the ratio in step 340 is less than the threshold, the refining of discriminant function F' is judged complete, and training phase 3 is concluded by passing control to step 342 where actual product inspection begins (step 400 in FIG. 2).

Figure 6:
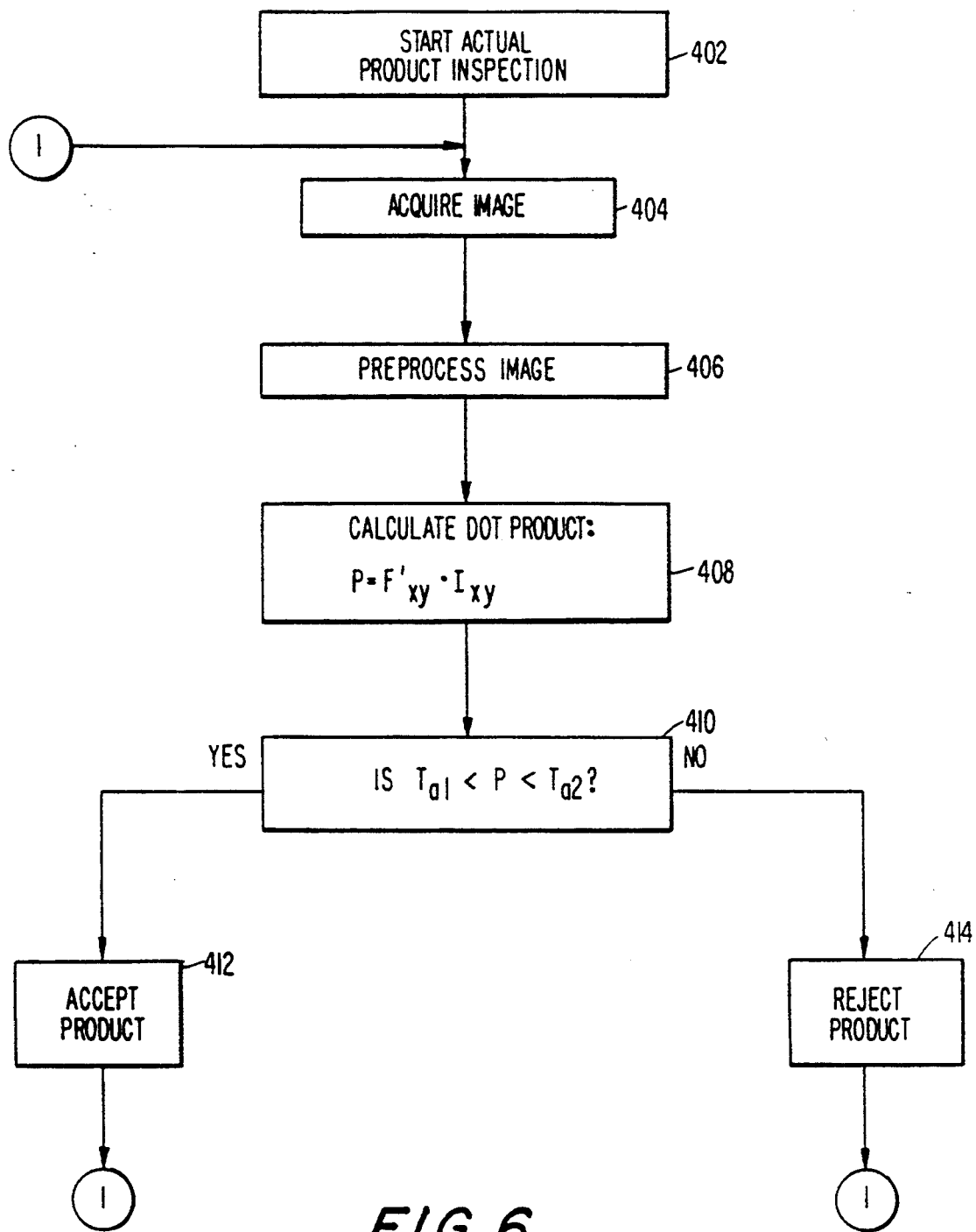
FIG. 6 is a flow chart of an illustrative, more detailed embodiment of yet another one of the steps shown in FIG. 2.

An illustrative embodiment of actual product inspection (step 400 in FIG. 2) is shown in FIG. 6. This process begins with step 402, and in step 404 an image is acquired as in step 206. In step 406 the data for this image is preprocessed as in step 208. In step 408 the dot product P of the refined discriminant function from training phase 3 and the image data from step 406 is calculated. In step 410 P is tested to determine whether or not it is in the range between the first threshold values from step 220. If so, the system deems the image acceptable and control passes to step 412 in order to accept the product (i.e., direct it to accepted product conveyor 20A in FIG. 1). If the step 410 test is not satisfied, the system deems the image unacceptable and control passes to step 414 in order to reject the product (i.e., direct it to rejected product conveyor 20R in FIG. 1). After either step 412 or 414, control returns to step 404 to begin processing of the next image.

The invention will now be further explained, by way of example.

EXAMPLE 1

FIG. 10 shows a model used to create a product gauge used in the inspection of rectangular packages. The rectangular package to be inspected partially consists of a package wrap, an artwork label, and a closure to hold the package together. A wooden or aluminum structure, the size, shape and weight of the rectangular package, serves as a model 504 used for the basis for a product gauge. Line markings on the model 504 outline the artwork areas 505, the areas where the package's wrap connects 506, and the area of the closure 507. All of these areas are important focus points for quality control since the assembly of this particular package allows independent movement of these components' positions. When the component's position is outside of certain limits, the package can be rejected as unacceptable.

The model 504 is placed on the conveyor system used to convey the products to be inspected. An image of the model that shows the model's line markings is captured by video cameras and is displayed on a video screen. This image constitutes the product gauge. The image of the model, the product gauge, is stored and presented on the video screen so that it is superimposed over the image of products that are to be inspected. An operator adjusts the conveyor system, camera systems and lighting systems in reference to the product gauge for optimum alignment for processing of information by the optical product inspection means. Adjustment is monitored by the operator via an operator interface partially comprised of the video monitor with a touch screen and/or a keyboard.

EXAMPLE 2

A model as described in Example 1 or an ideal or acceptable product is used as a model for the basis for a product gauge. The model is placed on the conveyor system used to convey the products to be inspected. As in Example 1, the image of the model is displayed on the video monitor.

Using the image of the model as a guide, the operator creates a product gauge via a commonly available line-drawing computer program that is resident in an operator interface comprised of the video screen, a computer and a keyboard. The outline of the model as well as artwork areas and important inspection points are delineated by making a drawing on the video screen using the line-drawing computer program. The resulting line drawing is the product gauge and is used for subsequent alignment and monitoring of the system.

An image of the product gauge will be superimposed on the video screen over the image of a product to be inspected. This enables the operator to compare the image of the product gauge with the image of the product. The operator can use this comparison to determine the correct alignment of the systems as well as whether the product is acceptable or rejectable. The product gauge delineates important areas on the image of the products to be inspected, thereby focusing the operator's attention on certain areas of the product.

EXAMPLE 3

In this example, a computer program is used to create a product gauge. The program aids in converting a three dimensional image of a model, such as the model of Example 2, into two dimensional data points via a warp process. These data points are used to create the product gauge. The resulting product gauge defines inspection zones of the product to be inspected. This product gauge provides consistent product gauges between operators, between machines, and between changes in products to be inspected because it is electronically created under standardizable conditions. This product gauge can also be transferred to other systems electronically, thereby further providing for consistent inspection between operators, machines and changes in products.

The product gauge created by this program is displayed on a video screen and overlays or is superimposed over a product from the production line. By comparing the image of the product gauge with the image of a product, the product gauge can be used to align the cameras, lighting and conveyor system as well as aid the operator in monitoring the system. This product gauge can also aid the operator in the training phase of the system or in selecting ideal, acceptable or rejectable products. It does this by highlighting or delineating important areas of the product that are to be inspected which aids the operator in making a comparison.

This program aids in the creation of a product gauge by using the method of camera calibration with respect to a "3D scene to a 2D projection" which has been described in "Digital Image Processing" by Gonzalez and Wintz. The program aids in converting the three dimensional image of a model into two dimensional data points. The Gonzalez and Wintz reference shows that in order to solve the three dimensional to two dimensional transformation matrix and make the conversion, six fiducial or registration points are required for a unique view.

Figure 11A:
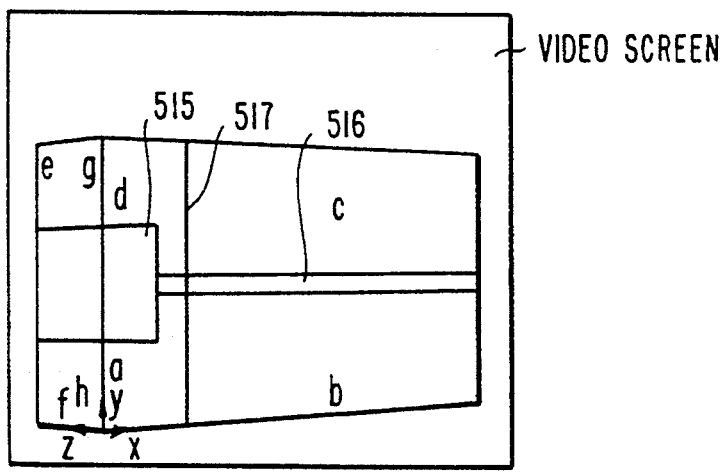
FIGS. 11a-11c (referred to collectively as FIG. 11) are embodiments of electronically drawn product gauges on video screens.
Figure 11B:
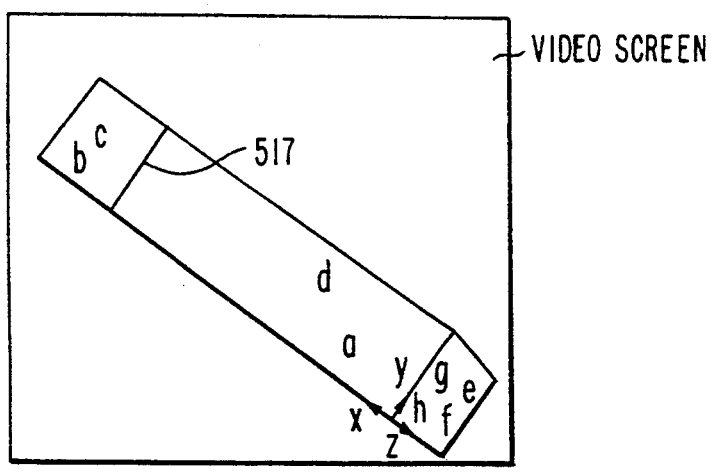
Figure 11C:
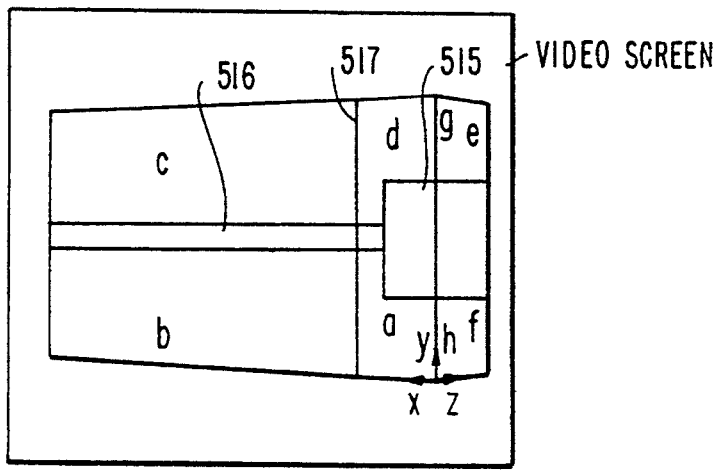

FIG. 11a, FIG. 11b, and FIG. 11c show an example of three product gauges representing three views and identify three dimensional fiducial points by letters. These product gauges can be produced by the program of this example. Eight fiducial points for each of the three views are presented. Line markings on the product gauges outline the package's artwork areas 515, the areas where the foil wrap connects 516 and the area of the closure 517. All of these areas are important focus points for quality control. The coordinates shown below represent the fiducial points and are in millimeters although this scale is arbitrary. They correspond to the fiducial points identified by letters in the views shown in FIG. 11a, FIG. 11b, and FIG. 11c.

|   | X | Y | Z |
|---|---|---|---|
| FRONT VIEW COORDINATES (FIG. 11a) | | | |
| a) | 4.35 | 11.40 | 0.00 |
| b) | 72.70 | 6.60 | 0.00 |
| c) | 67.00 | 42.00 | 0.00 |
| d) | 8.20 | 45.40 | 0.00 |
| e) | 0.00 | 49.10 | 16.70 |
| f) | 0.00 | 4.60 | 14.65 |
| g) | 0.00 | 49.40 | 5.25 |
| h) | 0.00 | 7.30 | 6.00 |
| SIDE VIEW COORDINATES (FIG. 11b) | | | |
| a) | 21.10 | 9.30 | 0.00 |
| b) | 92.30 | 4.600 | 0.00 |
| c) | 91.60 | 15.15 | 0.00 |
| d) | 35.00 | 18.10 | 0.00 |
| e) | 0.00 | 17.40 | 44.75 |
| f) | 0.00 | 4.40 | 49.60 |
| g) | 0.00 | 15.85 | 7.55 |
| h) | 0.00 | 6.00 | 4.60 |
| BACK VIEW COORDINATES (FIG. 11c) | | | |
| a) | 7.50 | 10.85 | 0.00 |
| b) | 68.20 | 5.50 | 0.00 |
| c) | 73.65 | 43.60 | 0.00 |
| d) | 11.00 | 44.45 | 0.00 |
| e) | 0.00 | 49.40 | 17.75 |
| f) | 0.00 | 7.30 | 17.00 |
| g) | 0.00 | 49.10 | 6.30 |
| h) | 0.00 | 4.60 | 8.35 |

The two dimensional values corresponding to the three dimensional data presented above are determined by the user at the time a model is presented to the imaging system of the optical product inspection means. Once the two dimensional values are determined, the coefficients of a transformation matrix are determined by solving a set of simultaneous equations using Gaussian elimination using these two dimensional values and the three dimensional coordinates. The coefficients of this matrix are used to transform the three dimensional coordinates describing the product gauge including the three dimensional coordinates of the inspection zones to two dimensional coordinates. These two dimensional coordinates are used to create a drawing which is the product gauge.

Figure 12A:
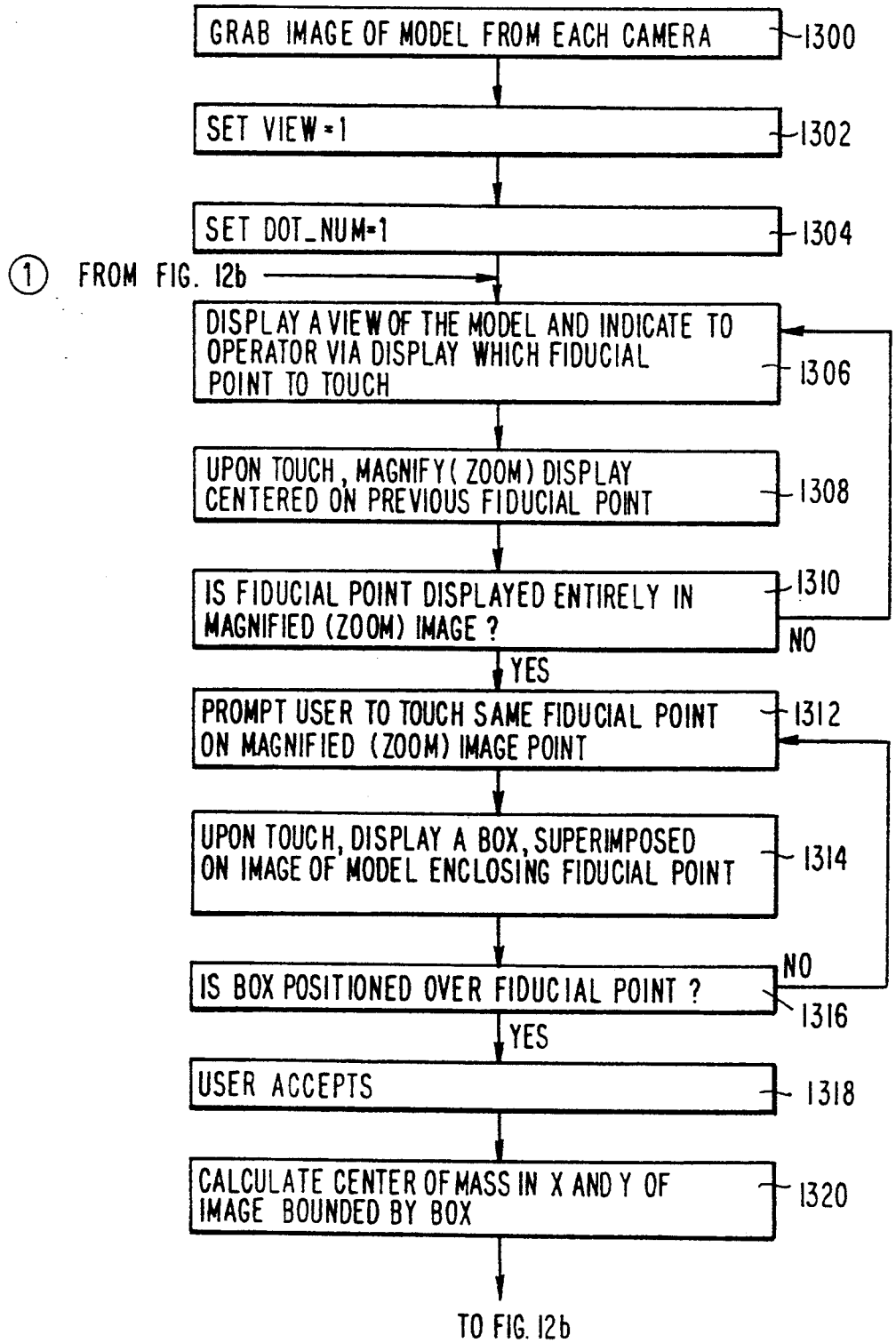
FIGS. 12a and 12b (referred to collectively as FIG. 12) are a flow chart for creating an illustrative embodiment of a product gauge.
Figure 12B:
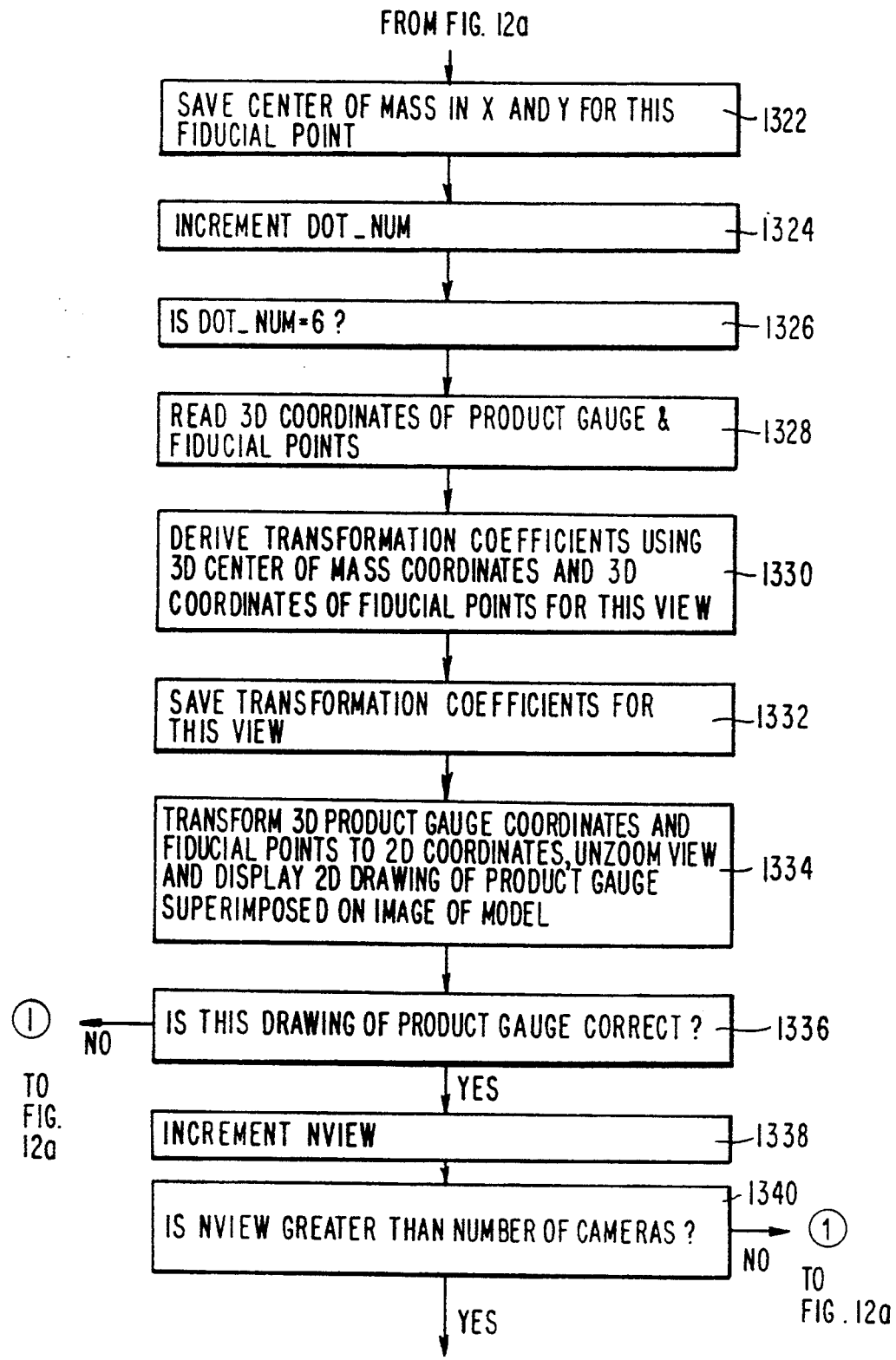

FIG. 12 is a flow chart of an illustrative, detailed embodiment of this example. The flow chart illustrates the steps used in a computer program to produce product gauges. The procedure was implemented on a personal computer employing a video monitor with a touch screen. The touch screen simplifies the identification of the six fiducial points on the image of the model. For each fiducial point identification, the user is required to touch the screen twice. The first touch is to identify which fiducial point is to be the input. The second touch is then performed on a magnified image centered on the first touch or first user input. The second input is used as an approximate center for a center-of-mass calculation. The fiducial point on the model is shown on the video monitor by a filled white circle. From the data available or computed, the computer produces a drawing, which is the product gauge. The product gauge can be superimposed over a product to be inspected on the video monitor.

In step 1300 of FIG. 12, the image of a model is acquired from a camera of the optical product inspection means. The model, as in Example 2, can consist of an ideal or an acceptable product or can consist of a physical representation of a product.

In step 1302 a VIEW parameter is set to one and in step 1304 a DOTNUM parameter is set to one. The VIEW parameter represents a particular view of the product (e.g., the product's top) and the DOTNUM parameter represents a particular fiducial point (e.g., uppermost left point on the product's top).

In step 1306, the image of the model is displayed on a video monitor that has a touch screen. The operator is directed to touch a particular fiducial point of the image of the model on the touch screen.

When the operator touches the fiducial point on the video monitor, in step 1308 a zoom or magnification of the area is displayed which is centered around the part of the image where the operator touched the video monitor.

In step 1310, the operator determines whether the fiducial point from step 1306 is positioned correctly in the magnified image of the model. If it is not, steps starting with 1306 are repeated. If it is positioned correctly, step 1312 directs the operator to touch the same fiducial point again, this time on the magnified display. Upon this touch, in step 1312, a box or rectangle image is displayed on the video monitor. The box image is superimposed over the image of the model and the box image encloses the fiducial point.

Step 1316 directs the operator to determine whether the box image is positioned over the fiducial point correctly. If it is not, steps starting with 1312 are repeated. If it is positioned correctly, then the fiducial point is acceptable for step 1318.

In step 1320 the two dimensional center of mass of the image of the model bounded by the box image is calculated. This center of mass calculation for this particular fiducial point is saved in step 1322.

After saving the center of mass calculation, the DOTNUM parameter is incremented one in step 1324. Steps 1306 through 1324 are repeated until DOTNUM=6 as shown in step 1326, thus providing six fiducial points for computation for each view. Six fiducial points per view is the minimum. Larger numbers of fiducial points could be chosen; six are used here for the purpose of illustration.

In step 1328 three dimensional coordinates previously calculated of the model along with the fiducial points are read. FIG. 11 shows examples of these three dimensional coordinates for a particular product. Eight fiducials for each of three views are shown in FIG. 11 for the purpose of illustration. As was stated, six fiducial points per view is the minimum. Larger numbers of fiducials along with different numbers of views could have been chosen. The particular product and the particular inspection desired should guide the number of fiducials and the number of views selected. Generally, the more complicated the shape of the product and the more demanding or thorough the inspection desired means that more fiducials and more views should be selected.

In step 1330 of FIG. 12, transformation coefficients are derived from these three dimensional coordinates, the fiducial points, and the two dimensional center of mass coordinates saved in step 1322 for the particular view. These transformation coefficients are saved for this particular view in step 1332.

In step 1334, these transformation coefficients are used to transform the three dimensional coordinates that were read in step 1328 into two dimensional coordinates. Also in this step, the view is unzoomed and a two dimensional drawing based on the two dimensional coordinates is displayed on the video monitor superimposed over the image of the model. This drawing is the product gauge.

The operator examines this image of the product gauge superimposed over the image of the model and determines, in step 1336, whether it is correct. If it is not, the process is repeated beginning with step 1306. If it is correct, VIEW is incremented one in step 1338. In step 1340, the steps beginning with step 1306 are repeated for a new view. If no more views are desired, the process is complete and a product gauge comprised of a drawing has been created for each desired view. Generally, one product gauge per camera view available is desired.

All three of the above examples of product gauges can be used with the optical inspection means of a product inspection apparatus. They aid in simplifying the set-up, increasing the efficiency of the apparatus, and increasing the applicability of any product inspection apparatus including simplifying and aiding in the changeover from inspecting one product to inspecting another. Thus, it is seen that this product gauge invention increases the performance of optical product inspection means and the overall performance of a product inspection apparatus.

It will be understood that the foregoing is merely illustrative of the principles of the invention, and that various modifications can be made by those skilled in the art without departing from the scope and spirit of the invention.

What is claimed is:

1. A method of determining the acceptability of a product, comprising the steps of:
   superimposing a product gauge image over an image of the product;
   identifying an acceptable image by comparing the product gauge image with the image of the product;
   generating a filter from a first set of acceptable images of said product;
   comparing said filter with a member of a second set of images of said product to produce a processed value, said second set including at least some acceptable images;
   repeating said comparing step to produce a distribution of processed values;
   generating from said distribution of processed values a first range (A) of processed values, said first range comprising processed values associated with acceptable images of said product;
   generating from said distribution of processed values a second range (B) of processed values, said second range comprising processed values associated with unacceptable images of said product;
   comparing said filter with a further image of said product so as to produce a further processed value;
   generating an indication of acceptability or unacceptability of said further image by comparing said further processed value to said first and second ranges;
   if said further processed value is outside both said first and second ranges, selecting said further image only if said further image is acceptable; and
   adaptively training said filter with said selected further image to produce a modified filter such that comparing said modified filter with said selected further image produces a modified processed value which is within said first range.

2. The method of determining the acceptability of a product of claim 1 wherein said product gauge image is an image of a model of the product.

3. The method of determining the acceptability of a product of claim 1 wherein the product gauge image is drawn on a video monitor.

4. The method of determining the acceptability of a product of claim 3 wherein the product gauge image is drawn using a computer program.

5. The method of determining the acceptability of a product of claim 4 wherein said product gauge image is drawn using a computer program which converts a three dimensional image of a model of the product into two dimensional data points via a warp process.

6. The method of determining the acceptability of a product of claim 1 wherein the product gauge image is adapted to aid in the alignment of components used in determining the acceptability of the product.

7. The method of determining the acceptability of a product of claim 1 wherein if a product is unacceptable the product gauge image is altered to indicate why.

8. The method of determining the acceptability of a product of claim 1 wherein said superimposing step comprises superimposing the product gauge image over the image of the product on a video monitor.

9. The method of determining the acceptability of a product of claim 1 further comprising superimposing the product gauge image over said further image and comparing the superimposed images to determine if said further image is acceptable.

10. The method of determining the acceptability of a product of claim 9 wherein said superimposing step comprises superimposing the product gauge image over said further image on a video monitor.

11. The method of determining the acceptability of a product of claim 8 wherein said product gauge image is an image of a model of the product.

12. The method of determining the acceptability of a product of claim 8 wherein said product gauge image is drawn on a video monitor.

13. The method of determining the acceptability of a product of claim 12 wherein the product gauge image is drawn using a computer program.

14. The method of determining the acceptability of a product of claim 13 wherein said product gauge image is drawn using a computer program which converts a three dimensional image of a model of the product into two dimensional data points via a warp process.

15. The method of determining the acceptability of the appearance of each of a plurality of products comprising the steps of:
 forming an image of each of a first subplurality of said products;
 superimposing a product gauge image over each of the images of said first subplurality;
 identifying acceptable in, ages by comparing the product gauge image with each of the images of the first subplurality;
 combining the images of said acceptable images to produce an initial discriminant function;
 forming an image of each of a second subplurality of said products;
 using said initial discriminant function to process each of the images of said second subplurality in order to produce a processed value for each of said images from said second subplurality which is indicative of how similar said image from said second subplurality is to said initial discriminant function;
 selecting first processed value thresholds between which a first majority of said processed values fall;
 selecting second processed value thresholds between which a second majority of said processes values fall, said second majority being larger than said first majority;
 forming an image of each of a third subplurality of said products;
 using selected images of said third subplurality to progressively refine said discriminant function by
 (1) using said discriminant function to process each successive image from said third subplurality in order to produce a processed value for said image from said third subplurality, (2) determining whether said processed value is substantially between said second value thresholds, and (a) if not, discarding said image from said third subplurality and skipping step (3) below, or (b) if so, determining whether said processed value is substantially between first processed value thresholds, and (i) if so, continuing with step (3) below, or (ii) if not, discarding said image from said third subplurality and skipping step (3) below unless said image from said third subplurality appears acceptable, and (3) modifying said discriminant function in accordance with said image from said third subplurality;
 forming an image of each of a fourth subplurality of said objects; and
 using the refined discriminant function to determine whether or not each of the images of said fourth subplurality has an acceptable appearance.

16. The method according to claim 15, wherein said step of using selected images comprises the additional steps at (2)(b)(ii) of superimposing the product gauge image over said image from said third subplurality and identifying acceptability of said image by comparing the product gauge image with said image.

17. The method according to claim 15, further comprising the step, if it is determined that an image of said fourth subplurality has an unacceptable appearance, of superimposing the product gauge image over this image and further identifying the image as acceptable or unacceptable by comparing the product gauge image with the image.

18. The method according to claim 17, wherein said step of using selected images comprises the additional steps at (2)(b)(ii) of superimposing the product gauge image over said in, age from said third subplurality and identifying acceptability of said image by comparing the product gauge image with said image.

19. The method of determining the acceptability of a product of claim 15 wherein said product gauge image is an image of a model of the product.

20. The method of determining the acceptability of a product of claim 15 wherein said product gauge image is drawn on a video monitor.

21. The method of determining the acceptability of a product of claim 20 wherein the product gauge image is drawn using a computer program.

22. The method of determining the acceptability of a product of claim 21 wherein said product gauge image is drawn using a computer program which converts a three dimensional image of a model of the product into two dimensional data points via a warp process.

23. The method according to claim 19 further comprising the step, if it is determined that an image of said fourth subplurality has an unacceptable appearance, of superimposing the product gauge image over this image and further identifying this in, age as acceptable or unacceptable by comparing the product gauge image with this image.

24. The method of determining the acceptability of the appearance of each of a plurality of products comprising the steps of:
 forming an image of each of a first subplurality of said products;
 combining the images of said first subplurality to produce an initial discriminant function;
 forming an image of each of a second subplurality of said products;

using said initial discriminant function to process each of the images of said second subplurality in order to produce a processed value for each of said images from said second subplurality which is indicative of how similar said image from said second subplurality is to said initial discriminant function;

selecting first processed value thresholds between which a first majority of said processed values fall;

selecting second processed value thresholds between which a second majority of said processed values fall, said second majority being larger than said first majority;

forming an image of each of a third subplurality of said products;

using selected images of said third subplurality to progressively refine said discriminant function by (1) using said discriminant function to process each successive image from said third subplurality in order to produce a processed value for said image from said third subplurality, (2) determining whether said processed value is substantially between said second value thresholds, and (a) if not, discarding said image from said third subplurality and skipping step (3) below, or (b) if so, determining whether said processed value is substantially between first processed value thresholds, and (i) if so, continuing with step (3) below, of (ii) if not, discarding said image from said third subplurality and skipping step (3) below unless said image from said third subplurality appears acceptable, wherein the acceptability of said image of said third subplurality is determined by superimposing a product gauge in, age over said image from said third plurality and identifying the acceptability of said image by con, paring the product gauge image with said image, and (3) modifying said discriminant function in accordance with said image from said third subplurality;

forming an image of each of a fourth subplurality of said products; and using the refined discriminant function to determine whether or not each of the images of said fourth subplurality has an acceptable appearance.

25. The method of determining the acceptability of a product of claim 24 wherein said product gauge image is an image of a model of the product.

26. The method of determining the acceptability of a product of claim 24 wherein said product gauge image is drawn on a video monitor.

27. The method of determining the acceptability of a product of claim 26 wherein the product gauge image is drawn using a computer program.

28. The method of determining the acceptability of a product of claim 27 wherein said product gauge in, age is drawn using a computer program which converts a three dimensional in, age of a model of the product into two dimensional data points via a warp process.

29. The method of processing a plurality of images to produce an image discriminant function comprising the steps of:

superimposing a desired gauge image over each of a plurality of images;

identifying acceptable images by comparing the superimposed desired gauge image with each of the plurality of images;

subdividing a first of said acceptable images into a plurality of pixels, each of which has an initial digital value proportional to a predetermined image characteristic of the associated portion of the associated image;

assigning a first numerical value to each pixel having an initial digital value which is on one side of a predetermined threshold value and assigning a second numerical value to each pixel having an initial digital value which is on the other side of said threshold value to produce an initial discriminant function;

subdividing each remaining acceptable image in said plurality of images into a plurality of pixels, each of which as an initial digital value proportional to said predetermined image characteristic of the associated portion of the associated image;

assigning said first numerical value to each pixel in each remaining acceptable image having an initial digital value which is on one side of said threshold value and assigning said second numerical value to each pixel in each remaining acceptable image having an initial digital value which is on the other side of said threshold value; and producing said image discriminant function by sequentially performing the logical OR operation between each of said remaining acceptable images after assigning said numerical values and the initial discriminant function, the result of each logical OR operation replacing said initial discriminant function for the next performance of said logical OR operation.

30. The method of determining the acceptability of a product of claim 29 wherein said superimposing step comprises superimposing the product gauge image over said further image on a video monitor.

31. The method of determining the acceptability of a product of claim 29 wherein said product gauge image is an image of a model of the product.

32. The method of determining the acceptability of a product of claim 31 wherein said product gauge image is drawn on a video monitor.

33. The method of determining the acceptability of a product of claim 32 wherein the product gauge image is drawn using a computer program.

34. The method of determining whether or not a sample image is substantially similar to a predetermined standard image comprising the steps of:

(a) forming a discriminant function which is representative of said standard image;

(b) comparing each or a first plurality of possible examples of said sample image to said discriminant function to produce a first processed value for each of said first plurality of examples of said sample image, each of said processed values being indicative of how similar the associated example is to said standard image;

(c) comparing a further possible example of said sample image to said discriminant function to produce a further processed value indicative of how similar said further example of said sample in, age is to said standard image;

(d) using said first processed values to at least partly determine whether said further possible example of said sample image is substantially similar to said standard in, age, and if so, modifying said discriminant function in accordance with said further example of said sample image;

(e) repeating steps (c) and (d) for each of a plurality of further possible examples of said sample image to progressively modify said discriminant function;

(f) comparing said sample image to the modified discriminant function to produce a sample processed value indicative of how similar said sample image is to said standard image, and if this comparison indicates that said sample image is not substantially similar to said standard image, performing the additional steps of;

(g) superimposing a standard gauge image over said sample image; and (h) comparing the superimposed standard gauge image to said sample image to determine if said sample image is substantially similar to said standard gauge image.

35. The method of determining the acceptability of a product of claim 34 wherein said superimposing step comprises superimposing the product gauge image over said further image on a video monitor.

36. The method of determining the acceptability of a product of claim 34 wherein said product gauge image is an image of a model of the product.

37. The method of determining the acceptability of a product of claim 36 wherein said product gauge image is drawn on a video monitor.

38. The method of determining the acceptability of a product of claim 37 wherein the product gauge image is drawn using a computer program.

* * * * *